(12) United States Patent
Davies et al.

(10) Patent No.: US 6,378,519 B1
(45) Date of Patent: *Apr. 30, 2002

(54) INHALATION DEVICE

(75) Inventors: Michael Birsha Davies, Ware; David John Hearne, Luton; Paul Kenneth Rand, Letchworth; Richard Ian Walker, Ware, all of (GB)

(73) Assignee: Glaxo Group Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/456,201

(22) Filed: Dec. 7, 1999

Related U.S. Application Data

(63) Continuation of application No. 09/166,557, filed on Oct. 5, 1998, now Pat. No. 6,032,666, which is a continuation of application No. 08/979,217, filed on Nov. 26, 1997, now Pat. No. 5,860,419, which is a division of application No. 08/467,469, filed on Jun. 6, 1995, now Pat. No. 5,873,360, which is a continuation of application No. 08/552,166, filed on Nov. 2, 1995, now Pat. No. 5,590,645, which is a continuation of application No. 08/175,174, filed on Dec. 28, 1993, now abandoned, which is a continuation of application No. 07/663,145, filed on Mar. 1, 1991, now abandoned.

(30) Foreign Application Priority Data

Mar. 2, 1990 (GB) .............................................. 9004781

(51) Int. Cl.[7] ............................................ A61M 15/00
(52) U.S. Cl. ............................. 128/203.21; 128/203.15
(58) Field of Search ....................... 128/203.15, 203.21; 604/58

(56) References Cited

U.S. PATENT DOCUMENTS

| | | | |
|---|---|---|---|
| 4,307,734 A | * 12/1981 | Blankenship | 131/329 |
| 4,627,432 A | * 12/1986 | Newell et al. | 128/203.15 |
| 4,668,218 A | * 5/1987 | Viertanen | 604/58 |
| 4,811,731 A | * 3/1989 | Newell et al. | 128/203.15 |
| 4,860,740 A | * 8/1989 | Kirk et al. | 128/203.15 |
| 5,020,527 A | * 6/1991 | Dessertine | 128/200.23 |
| 5,033,463 A | * 7/1991 | Cocozza | 128/203.21 |
| 5,035,237 A | * 7/1991 | Newell et al. | 128/203.15 |
| 5,372,128 A | * 12/1994 | Haber et al. | 128/203.21 |
| 5,590,645 A | * 1/1997 | Davies et al. | 128/203.15 |
| 5,860,419 A | * 1/1999 | Davies et al. | 128/203.15 |
| 5,873,360 A | * 2/1999 | Davies et al. | 128/203.15 |
| 6,032,666 A | * 3/2000 | Davies et al. | 128/203.15 |

FOREIGN PATENT DOCUMENTS

| | | | |
|---|---|---|---|
| AU | 089046531 | * 5/1991 | 604/58 |
| EP | 0239802 | * 10/1987 | 128/203.15 |
| EP | 0469814 | * 2/1992 | 128/203.15 |
| EP | 0558879 | * 9/1993 | 128/203.21 |
| FR | 2516387 | * 5/1983 | 128/203.15 |
| FR | 2667190 | * 4/1992 | 128/203.15 |
| GB | 2166957 | * 5/1966 | 128/203.15 |
| GB | 2108390 | * 5/1983 | 128/203.15 |
| GB | 2122903 | * 1/1984 | 128/203.15 |
| GB | 2179260 | * 3/1987 | 128/203.15 |
| WO | WO 92/05824 | * 4/1992 | 128/203.15 |

\* cited by examiner

Primary Examiner—Aaron J. Lewis
(74) Attorney, Agent, or Firm—Darby & Darby

(57) ABSTRACT

An inhalation device is described for use with a medicament pack in which at least one container for medicament in powder form is defined between two sheets peelably secured to one another. The device comprises means for peeling the sheets apart at an opening station to open the container; and an outlet, communicating with the opened container, through which a user can inhale medicament in powder form from the opened container.

26 Claims, 21 Drawing Sheets

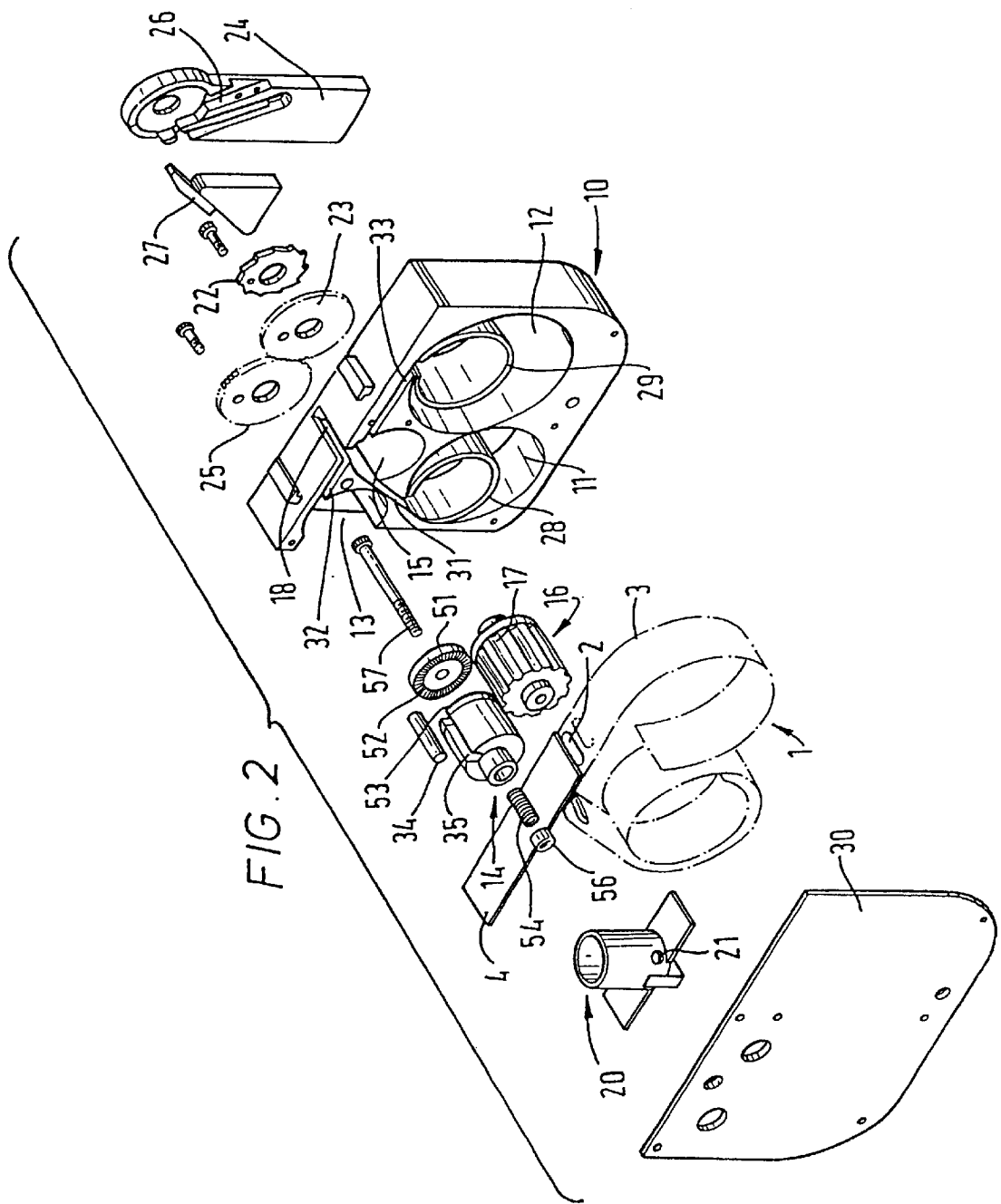

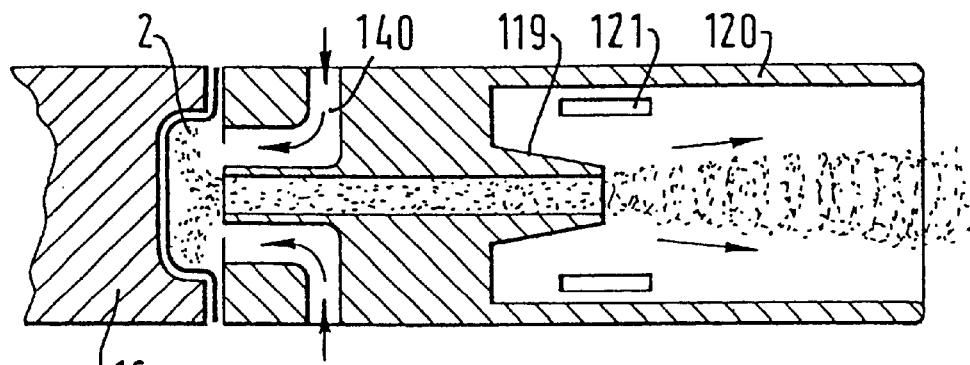
FIG. 4a
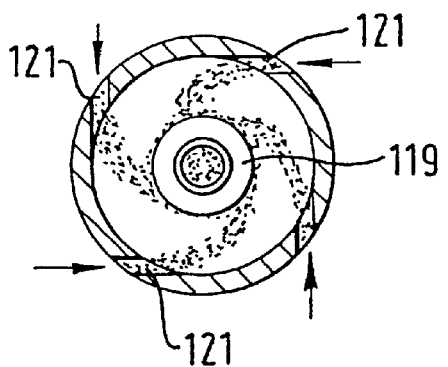
FIG. 4b
FIG. 5
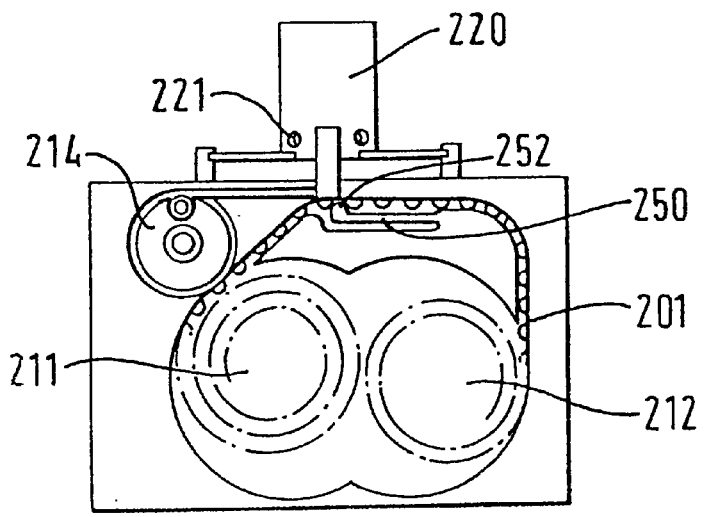

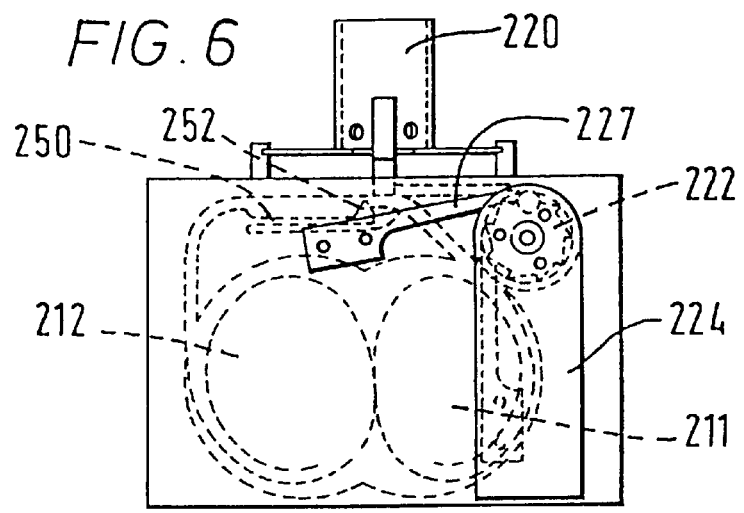
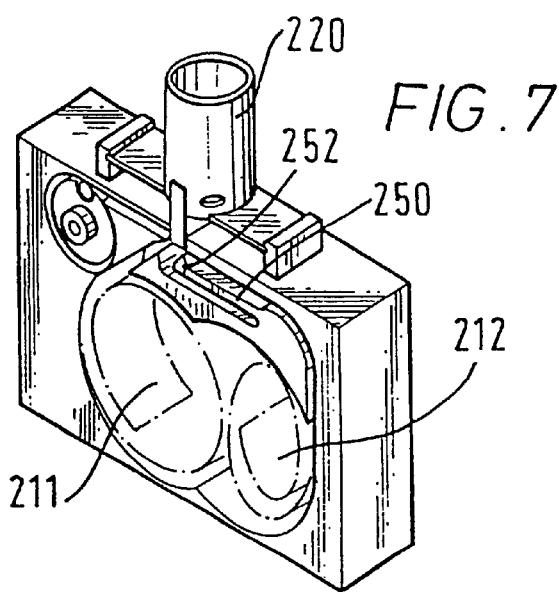
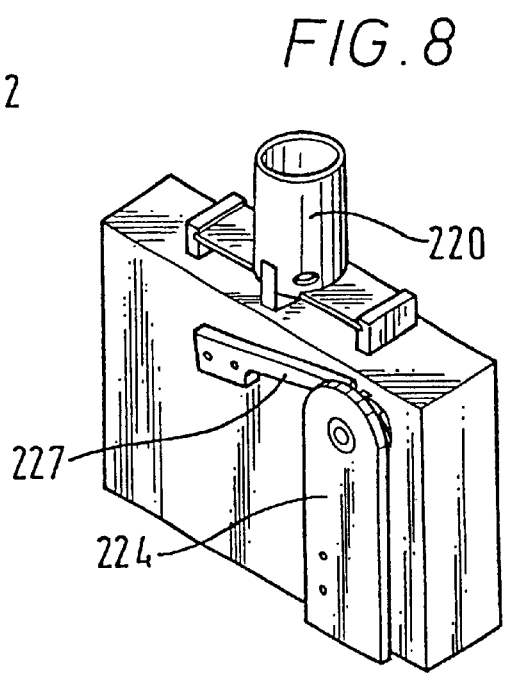

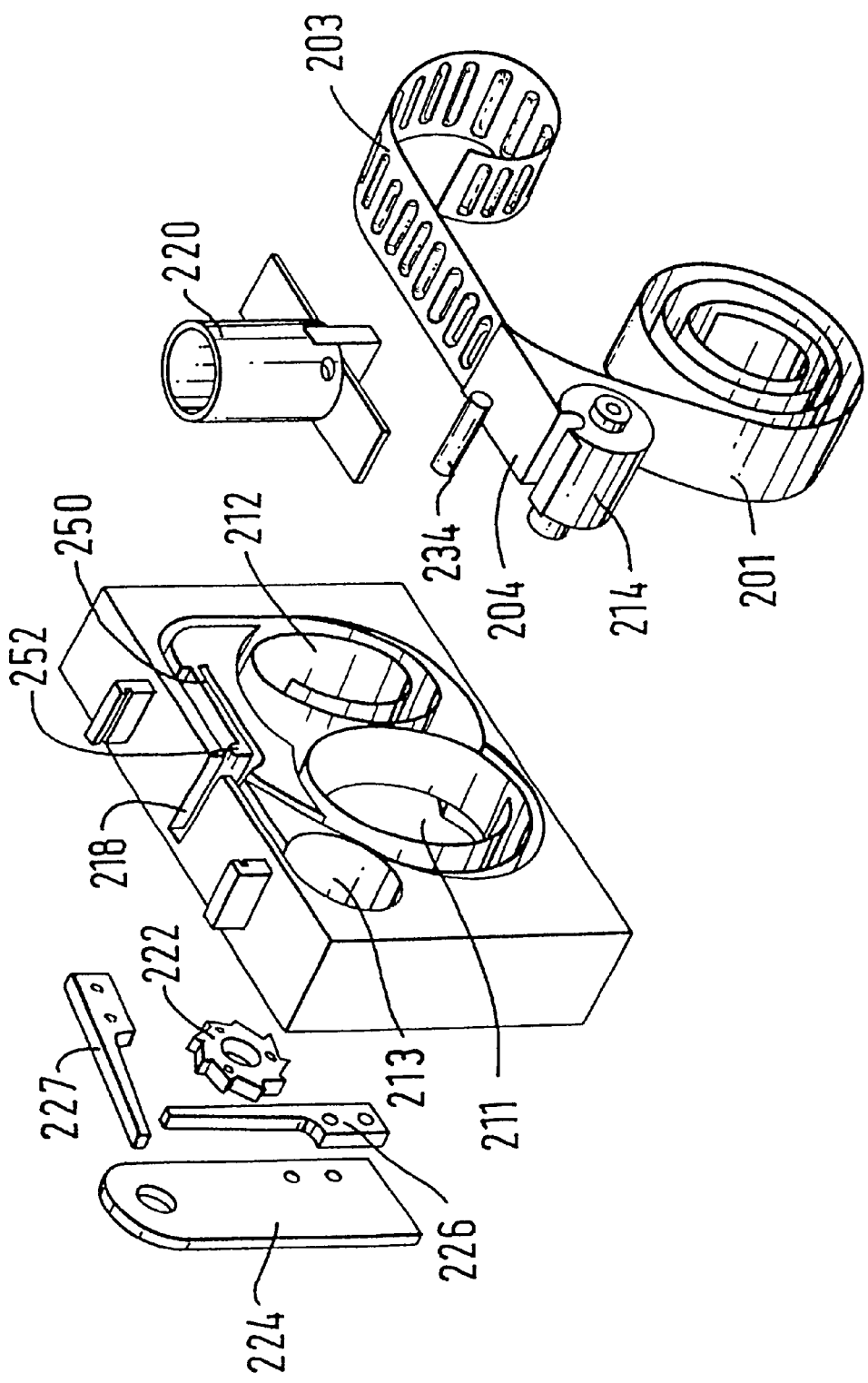

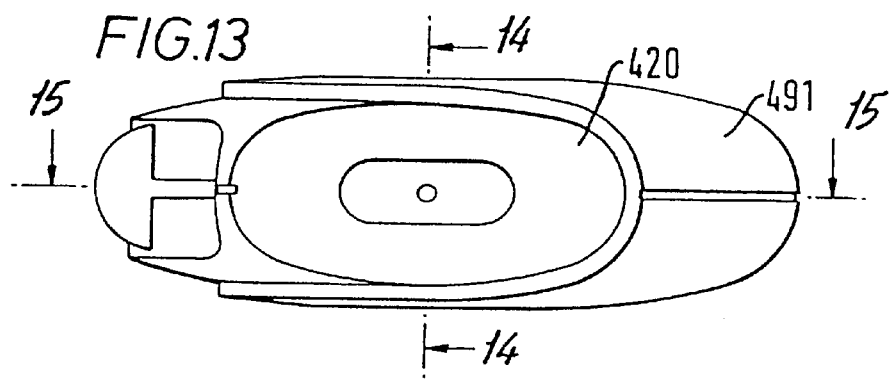
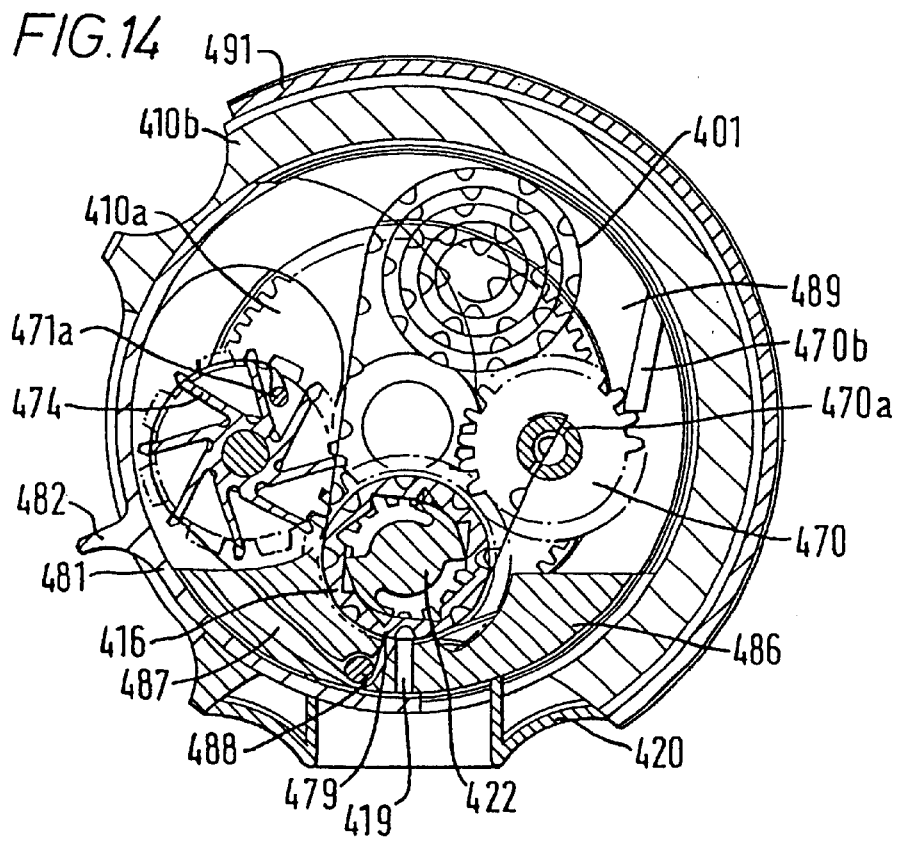
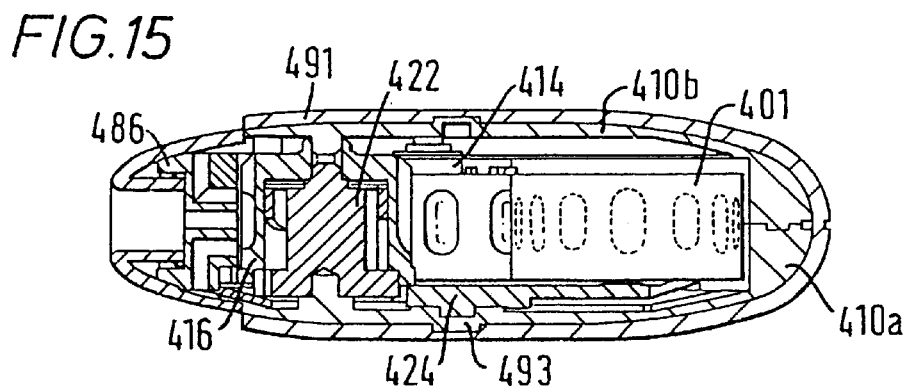

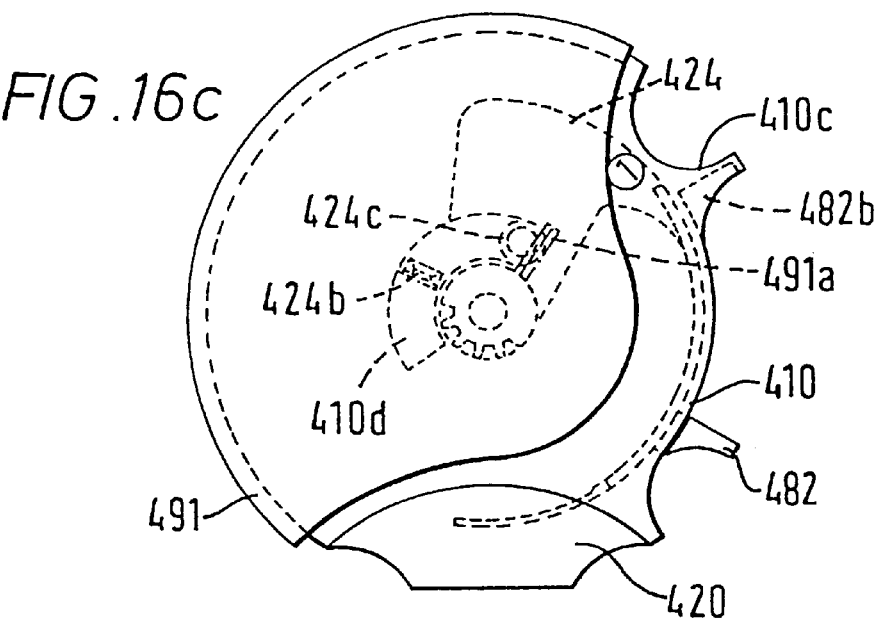
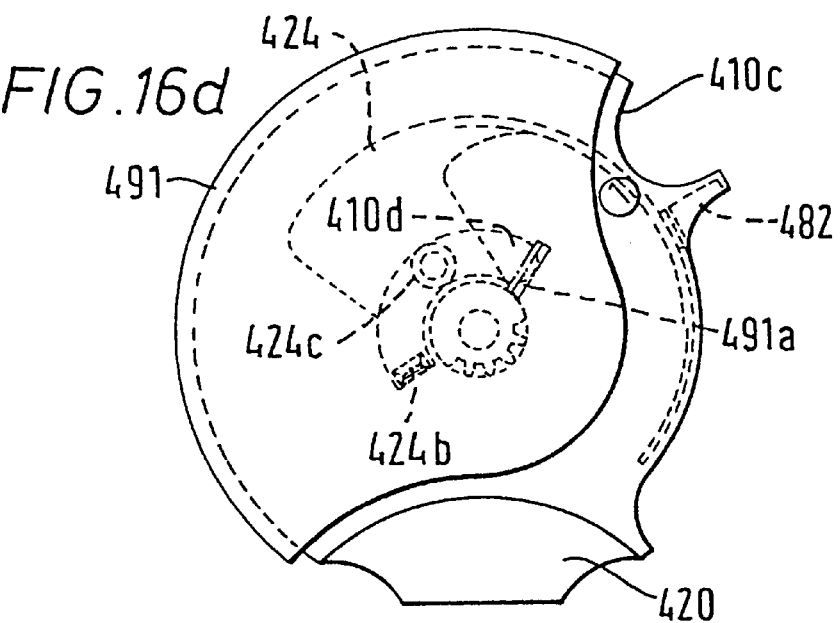
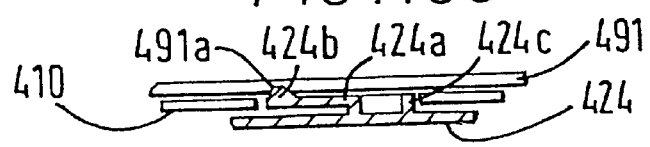

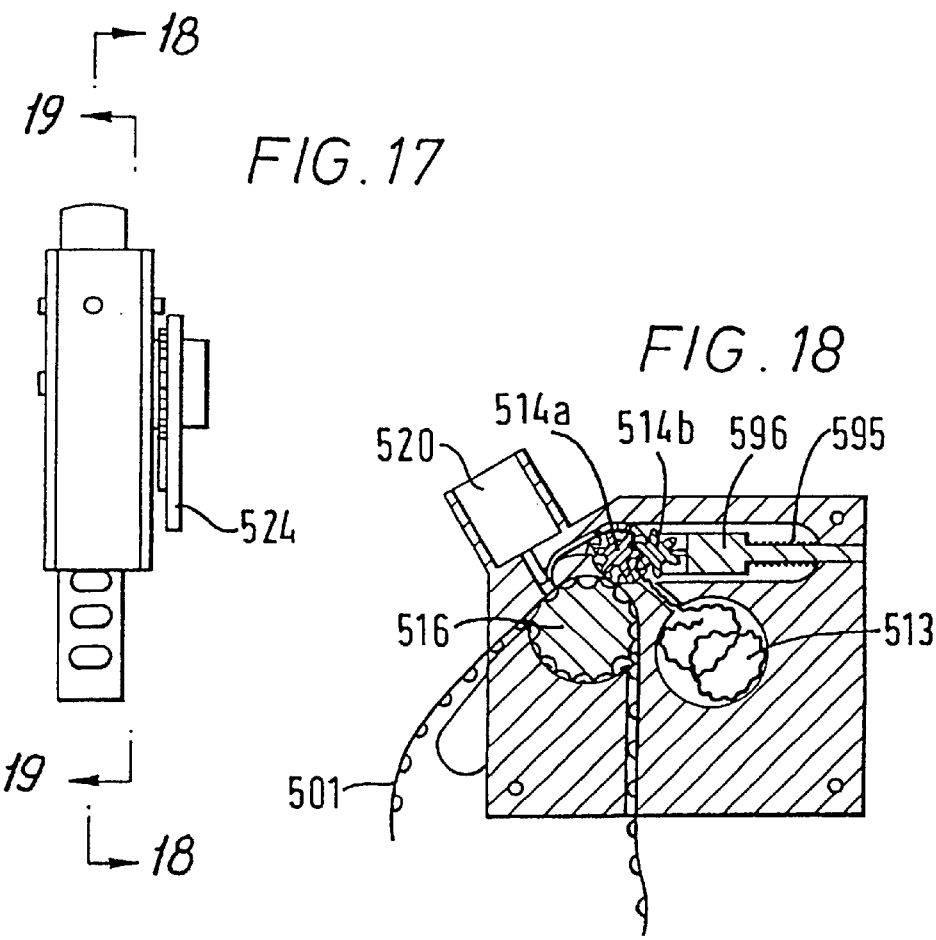
FIG. 17
FIG. 18
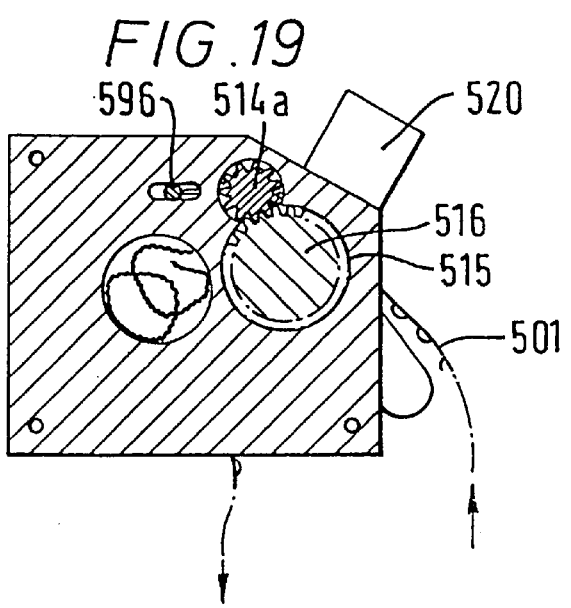
FIG. 19

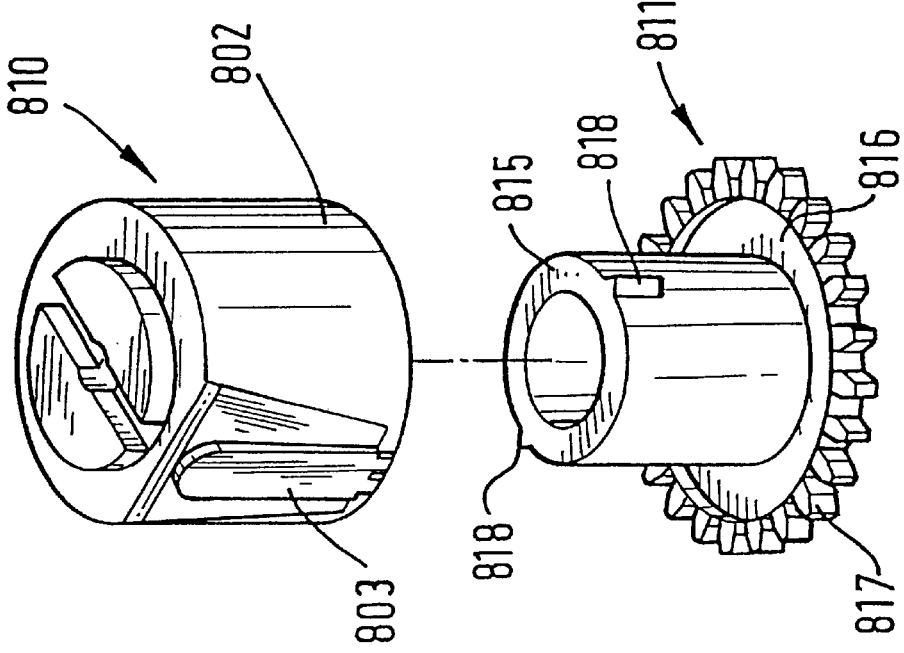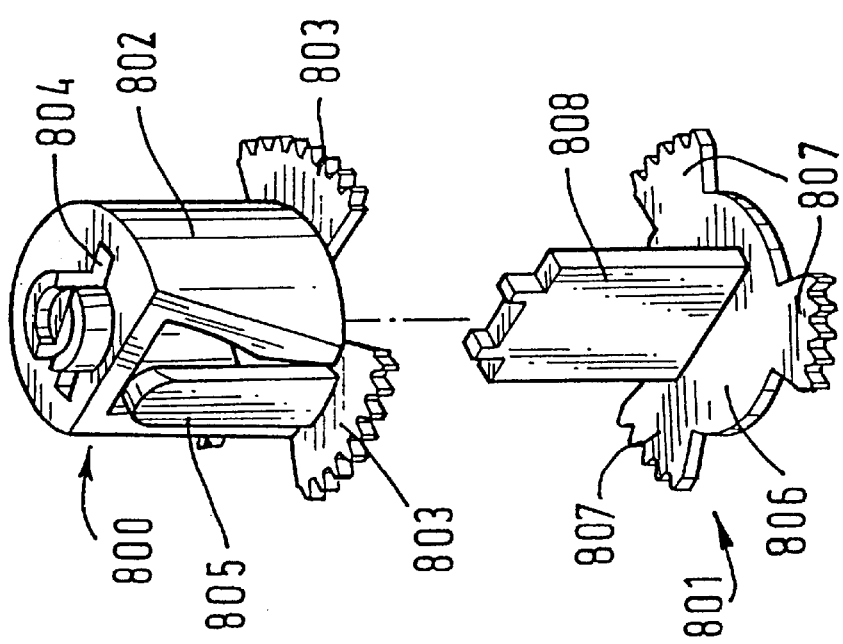

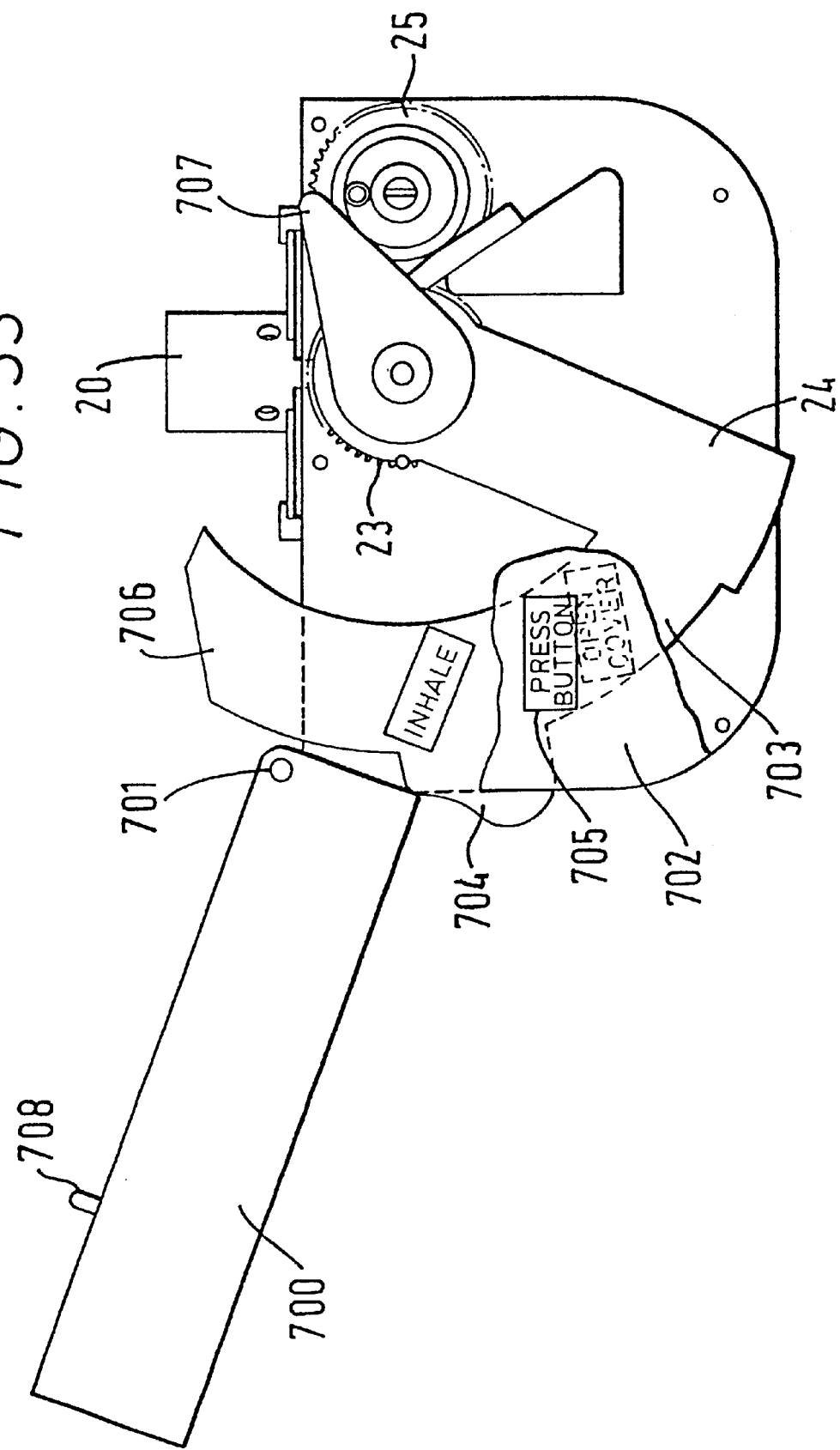

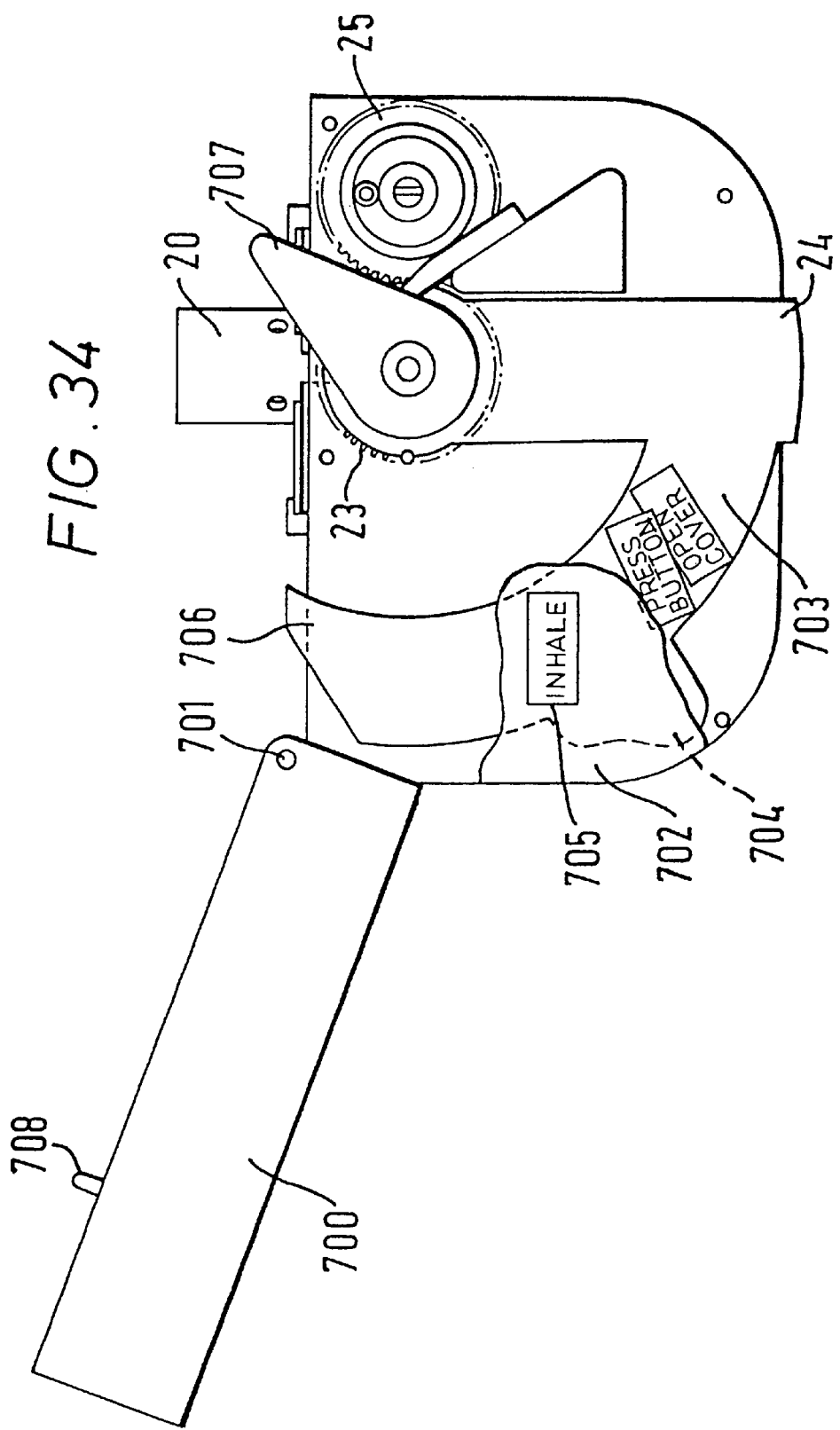

US 6,378,519 B1

INHALATION DEVICE

This is a continuation, of application Ser. No. 09/166,557, filed Oct. 5, 1998, now U.S. Pat. No. 6,032,666; which is a continuation of Ser. No. 08/979,217, filed Nov. 26, 1997, now U.S. Pat. No. 5,860,419, issued Jan. 19, 1999; which is a divisional of Ser. No. 08/467,469, filed Jun. 6, 1995, now U.S. Pat. No. 5.873,360, issued Feb. 23, 1999; which is continuation of Ser. No. 08/552,166, filed Nov. 2, 1995, now U.S. Pat. No. 5,590,645 issued Jan. 7, 1997; which is a continuation of Ser. No. 08/175,174, filed Dec. 28, 1993, now abandoned; which is a continuation of Ser. No. 07/663,145, filed Mar. 1, 1991, now abandoned. Each of these prior applications is hereby incorporated herein by reference, in its entirety.

FIELD AND BACKGROUND OF THE INVENTION

This invention relates to an inhalation device by means of which a user can inhale medicament in the form of a powder.

Inhalation devices are known for use with blister packs in which the medicament is held in powder form in the blisters thereof. Such devices include a puncturing member which punctures each blister in turn, thus enabling the medicament to be inhaled therefrom.

It is an object of the present invention to provide an inhalation device the design of which has the potential, if desired, to handle a medicament pack having a large number of discrete unit doses, without the device becoming unacceptably large.

BRIEF SUMMARY OF THE INVENTION

According to the present invention there is provided an inhalation device for use with a medicament pack in which at least one container for medicament in powder form is defined between two members peelably secured to one another, the device comprising means defining an opening station for the said at least one container; means for peeling the members apart at the opening station to open the container; and an outlet, communicating with the opened container, through which a user can inhale medicament in powder form from the opened container.

Preferably the medicament pack is formed from two elongate sheets which define a plurality of medicament containers spaced along the length thereof, means being provided for indexing each container in turn to the opening station.

The invention also provides a medicament pack for use in an inhalation device, the pack comprising an elongate strip formed from a base sheet having a plurality of recesses spaced along its length and a lid sheet hermetically but peelably sealed thereto to define a plurality of containers, each container having therein inhalable medicament in powder form. The strip is preferably sufficiently flexible to be wound into a roll.

BRIEF DESCRIPTION OF THE DRAWINGS

FIG. 2 is an axonometric exploded view of the components of the embodiment of FIG. 1;

FIGS. 4a and 4b are an axial section and cross-section respectively, on a larger scale than FIGS. 1 and 2, of a mouthpiece which may be used in the first embodiment (or in some other embodiment);

FIG. 5 is a front view of a second embodiment, with a cover thereof removed to show the interior;

FIG. 6 is a rear view of the second embodiment, but showing the interior thereof FIG. 7 is an axonometric front view of the second embodiment;

FIG. 8 is an axonometric .rear view of the second embodiment;

FIG. 9 is an axonometric exploded view of the second embodiment;

FIGS. 13 to 16 show a fourth embodiment of the invention, FIG. 13 being an underplan view, FIG. 14 a section on line A—A in FIG. 13, FIG. 15 a section on line B—B in FIG. 13, and FIG. 16 an exploded view-on a smaller scale;

FIGS. 16a to 16d show the fourth embodiment in successive stages of operation, and FIG. 16e is a section taken on line A—A in FIG. 16a;

FIGS. 17 to 20 show a fifth embodiment of the invention, FIG. 17 being an end view, FIG. 18 a section on line A—A in FIG. 17, FIG. 19 a section on line B—B in FIG. 17, and FIG. 20 an exploded view;

FIG. 30 is an exploded perspective view showing a further embodiment of clutch which may be used;

FIG. 31 is an exploded perspective view of yet another embodiment of clutch which may be used;

FIGS. 32 to 34 show successive positions of operation of another embodiment of the invention, in rear view.

DESCRIPTION OF PREFERRED EMBODIMENTS

Figure 1:
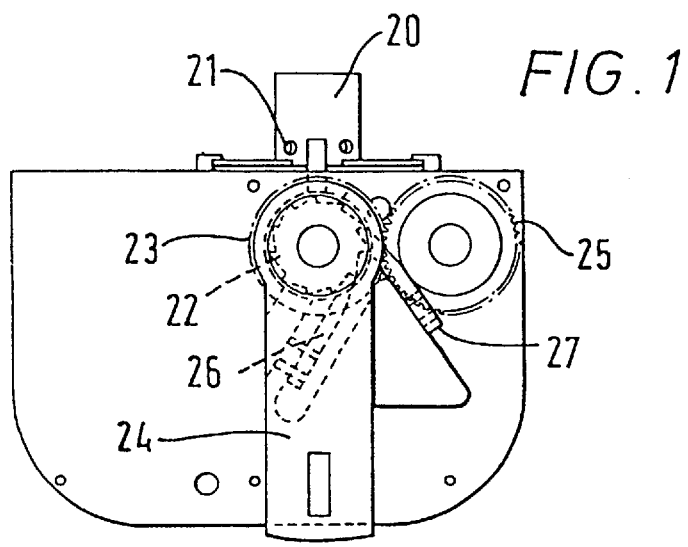
FIG. 1 is a rear view of a first embodiment of the invention.
Figure 3B:
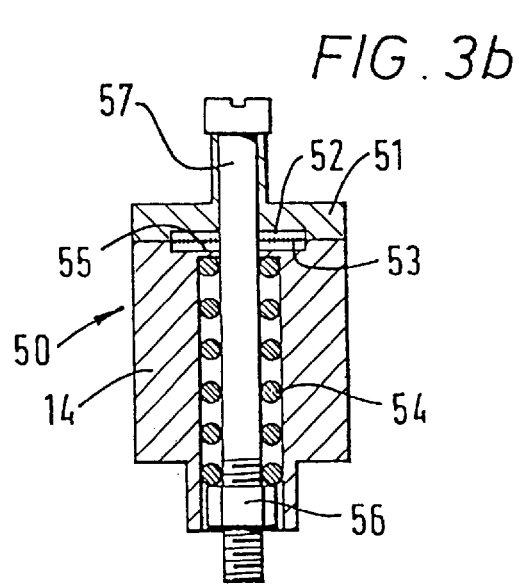
FIGS. 3a, 3b and 3c are an axonometric view, a longitudinal section and an end view (partly broken away) showing a clutch used in the embodiment of FIGS. 1 and 2.
Figure 3A:
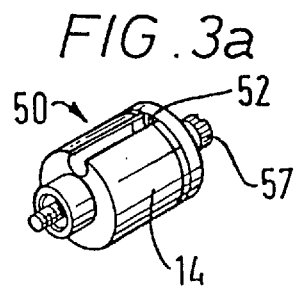
Figure 3C:
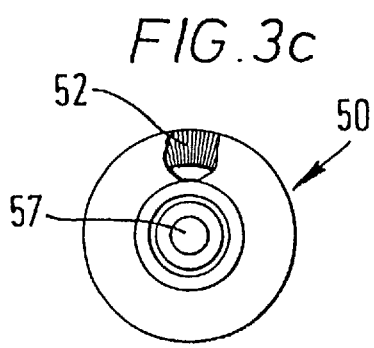

Referring now to FIGS. 1, 2 and 3a to 3c, these show an inhalation device in which is mounted a flexible strip 1 defining a plurality of pockets 2 each of which contains a dose of medicament which can be inhaled, in the form of a powder. The strip 1 comprises a base sheet 3 in which blisters are formed to define the pockets 2, and a lid sheet 4 which is hermetically sealed to the base sheet 3 except in the region of the blisters, in such a manner that the lid sheet and the base sheet can be peeled apart. The sheets are sealed to one another over their whole width except for leading end portions thereof where they are preferably not sealed to one another at all. The lid and base sheets are each preferably formed of a plastics/aluminium laminate, and the lid and base sheets are preferably adhered to one another by heat sealing. By way of example, the lid material may be a laminate consisting of 50 gsm bleach kraftpaper/12 micron polyester (PETP) film/20 micron soft temper aluminium foil/9 gsm vinylic peelable heat seal lacquer (sealable to PVC), and the base material may be a laminate consisting of 100 micron PVC/45 micron soft temper aluminium foil/25 micron orientated polyamide. The lacquer of the lid material is sealed to the PVC layer of the base material to provide the peelable seal between the lid and base sheets.

The strip 1 is shown as having elongate pockets which run transversely with respect to the length of the strip. This is convenient in that it enables a large number of pockets to be provided in a given strip length. The strip may, for example, be provided with sixty or one hundred pockets, but it will be understood that the strip may have any suitable number of pockets.

The inhalation device comprises a body 10 defining three storage chambers, namely a chamber 11 in which the strip 1 is initially housed and from which it is dispensed, a chamber 12 for receiving the used portion of the base sheet 3, and a chamber 13 within which the used portion of the lid sheet can be wound up on a wheel 14. The chambers 11 and 12 contain respective curved leaf springs 28 and 29, the purpose of which is described below. The body defines a further chamber 15 which houses an index wheel 16. This has a plurality of grooves 17 extending parallel to the axis of the wheel 16. The grooves are spaced at a pitch which is equal to the distance between the centre lines of adjacent pockets 2. The chambers 11, 12, 13 and 15 are closed by a lid 30. The chamber 15 communicates with the chambers 11, 12 and 13 via passages 31, 33 and 32 respectively.

The chamber 15 communicates via a slit 18 which, in turn, extends upwardly within a mouthpiece 20. The slot 18 also communicates with air inlets, as will be described below with reference to the specific mouthpiece shown in FIGS. 4a and 4b. The mouthpiece 20 is provided with additional air inlets 21 shown here in the form of a pair of circular apertures, though they may be of some other shape, as they are in FIGS. 4a and 4b. The primary purpose of the additional air inlets 21 is to provide additional air to the user and thus reduce the resistance to inhalation, though they may serve one or more additional purposes, as they do in FIGS. 4a and 4b and as is described below with reference to those Figures.

A means is provided by which the user can rotate the index wheel and the lid wheel in steps of a predetermined size. This means comprises a ratchet wheel 22.and a gear wheel 23, both connected to rotate in unison with the index wheel 16, a lever 24 arranged to rotate about the same axis as the ratchet wheel 22 and gear wheel 23, but independently thereof, and a gear wheel 25 which meshes with the gear wheel 23 and is arranged to rotate the lid wheel 14. The lever 24 carries a pusher arm 26, the end of which is arranged to engage the teeth of the ratchet wheel 22. The teeth of the ratchet wheel are also engaged by a pawl 27 fixedly secured to the body 10. For reasons which will become apparent from the description below of the operation of this embodiment, the gear wheel 25 is not connected directly to the lid wheel 14, but is connected via a slipping clutch 50 which is housed within the lid wheel 14. The effect of the provision of this clutch is that slipping occurs between the lid wheel and the gear wheel 25 when the force required to rotate the lid wheel exceeds a predetermined amount.

The clutch 50 comprises a disc 51 provided with radially extending serrations 52, or other surface roughness, which is held in engagement with a similarly serrated or roughened surface 53 provided on an end face of the lid wheel 14 by a compression spring 54. The spring 54 bears at one end against an inwardly directed surface 55 of the lid wheel and at the other end against a nut 56 threaded on a bolt 57.

The device described above can be made so as to be reusable after the doses of medicament contained in the pockets 2 have all been dispensed. In that: case, provision can be made for the user to gain access to the interior of the device, for example by removing the lid 30, so as to insert therein a fresh strip 1, for example in a cassette. Alternatively, however, the device may be made to be disposable once the strip 1 with which it is supplied has been used up.

In either event, when the device is first used the bulk of the strip 1 is within the chamber 11, kept in a relatively tight reel by the leaf spring 28, with a short portion at the leading end thereof passing out of the chamber 11 through the passage 31 to the index wheel 16. The foremost part of the leading end of the strip is peeled apart so that the leading end of the lid sheet 4 can be secured to the lid wheel 14, and so that the leading end of the base sheet 3 can enter the passage 33. The end of the lid sheet 4 is held in place on the lid wheel 14 by means of a key 34 which is a force fit in a slot 35 in the wheel 14.

A user desiring to use the device pushes the lever 24 in an anticlockwise direction, as viewed in FIG. 1, so that the pusher arm 26 urges the ratchet wheel 22 through an angle equal to the angular distance between two adjacent teeth. This causes the ratchet wheel 16 to rotate by an angular amount equal to the pitch of the groove 17 thereof and thus equal to the distance between two adjacent pockets 2 in the strip 1. This brings a pocket 2 opposite the slot 18 in the body 10. Since the ratchet wheel 22 and gear wheel 23 move unison, and since the gear wheel 25 meshes with the gear wheel 23, movement of the lever 24 also causes the lid wheel 14 to rotate. This peels a sufficient portion of the lid sheet 4 away from the base sheet 3 to expose the contents of the pocket 2 which is being brought into alignment with the slot 18.

When the user inhales through the mouthpiece 20 the flow of air which this produces entrains powder from the opened pocket, so that the powder is inhaled by the user. One way in which this can occur is explained in more detail below with reference to the embodiment of mouthpiece shown in FIGS. 4a and 4b. Each time the above procedure is repeated a further length of lid sheet is wrapped around the lid wheel 14 and a further length of base sheet enters chamber 12 through passage 33. The leaf spring 29 therein ensures that the base sheet is coiled up and does not snag on the wall of the chamber 12.

One effect of winding up the lid sheet on the lid wheel 14 is that the external diameter of the wheel plus the sheet wound thereon gradually increases. Were it not for the use of a slipping clutch to connect the gear wheel 25 to the lid wheel 14 this would have the result that successive operations of the lever 24 would try to cause a progressively longer length of lid sheet to be wound on to the lid wheel. The slipping clutch 50, however, avoids this effect, the clutch slipping each time by an amount sufficient to ensure that for every operation of the lever the amount of lid sheet wound on is precisely equal to the pitch of the pockets 2.

FIGS. 4a and 4b show a portion of the index wheel 16 with a pocket 2 therein, in conjunction with a mouthpiece which differs slightly from the mouthpiece 20 shown in FIGS. 1 to 3, and which is denoted by reference numeral 120. The mouthpiece 120 has air inlets 140, to which reference in general terms has already been made in connection with FIGS. 1 to 3, and a central powder outlet 119, one end of which is open to the pocket 2 and the other end of which opens into the interior of the mouthpiece 120.

When a user inhales through the mouthpiece 120 this causes air to flow in through the inlets 140 and thence through the pocket 2, into the powder outlet 119, and out through the mouthpiece, 120. By thus directing the flow of air through the pocket 2, efficient entrainment of powder in the airflow is achieved, with consequent efficient emptying of the pocket. The mouthpiece 120 is provided with additional air inlets 121, shown here by way of example as being four in number, which open tangentially into the mouthpiece. When the user inhales air is drawn into the mouthpiece not only through the air inlets 140 but also through the air inlets 121, and the air entering through the inlets 121 produces a swirling airflow which helps to distribute powder effectively within the airflow and reduce the extent to which powder is deposited on the inside of the mouthpiece. This also helps to break up any aggregates of powder which may be present in the blister.

An alternative clutch arrangement is shown in FIGS. 25 to 29. In this, the index, wheel 16 and the lid wheel 14 have respective toothed gear wheels 63 and 64 secured to them for rotation therewith. The direction of rotation is indicated by arrows in FIG. 27.

Gear wheel 63 has a toothed surface 65, with the teeth being provided continuously all the way round the surface 65 and at a constant pitch. By contrast, the gear wheel 64 has a toothed surface 66 from which some teeth are missing by virtue of the provision of radially extending slots 67. The circumferential width of each slot at the surface 66 is equal to one tooth pitch. The drawings show three such slots, but it should be understood that there could instead be one slot, two slots, or more than three slots. To one side of each of the slots 67, in fact upstream of each slot as considered in the direction of rotation of the gear wheel 64, a toothed section 68 is defined between the slot 67, and a narrow slit 69. The radially inner end of each slit 69 communicates with an aperture 70, so that each toothed portion 68 is connected to the remainder of the gear wheel 64 only by an arm 71. The gear wheel 64, or at least those portions thereof which provide the arms 71, is made of a material which permits the toothed portions 68 to flex resiliently back and forth in a circumferential direction. The rest position of the portions 68 is as shown in the drawings, but when a force is applied to a portion 68 in the direction of rotation of the gear wheel 64, the portion 68 can move so as to close the gap 67 at the radially outer end. This has the effect that a tooth is then "missing" not at the end of the slot 67 but at the end of the slit 69.

When the circumferential force applied by the gear wheel 63 to the gear wheel 64 is below a predetermined level the toothed portions 68 remain in their rest positions and the gear wheel 64 behaves just as if it had a continuous toothed surface like that of gear wheel 63. However, if the load exceeds a predetermined value, each time a toothed section 68 meshes with the gear wheel 63 it is moved circumferentially to close up the slot 67 at its outer end and open the slit 69. This movement of the toothed section 68 by a distance equal to the tooth pitch has the effect of producing slippage of the gear wheel 64 with respect to the gear wheel 69 equal to one tooth pitch. In this way, the illustrated arrangement is able to permit a total slippage of the gear wheels with respect to one another by a maximum of a distance equal to three times the tooth pitch per revolution, and hence a corresponding slippage of the lid wheel and index wheel with respect to one another. As will be appreciated, providing more or fewer toothed sections than the three illustrated will permit more or less than this maximum slippage.

A second embodiment of the inhalation device according to the invention is shown in FIGS. 5 to 9. This is intended for use with a strip 201, similar to the strip 1 used in the first embodiment except as regards the spacing of the pockets (for which see below). In many respects the second embodiment resembles the first embodiment,.and components in the second embodiment which correspond in general terms to particular components in the first embodiment are denoted by the same reference numerals, but with the addition of 200. The main difference between the first embodiment and the second embodiment is that in the latter there is no index wheel corresponding to the index wheel 16 of the first embodiment. Instead, indexing of the strip 1, to ensure that each operation of the lever advances the strip by an amount equal to the pitch of the pockets, is achieved by a resiliently flexible arm 250 terminating in a tooth 252 which engages between adjacent pockets. Each time the lever 224 is operated the arm 250 is resiliently depressed as a pocket slides past the tooth 252 thereof, and the tooth then springs back into engagement with the strip to the rear of the pocket which has just passed it.

It will be appreciated that, as in the case of the first embodiment, the diameter of the lid wheel 214 with the lid sheet thereon gradually increases during operation. Since a slipping clutch cannot be used in this embodiment the effect just described is compensated by having the spacing of the pockets 2 gradually increasing towards the rear end of the strip.

One other difference which will be noted between the first and second embodiments, is that in the latter the chambers 211 and 212 form a single composite chamber, unlike the separate chambers 11 and 12 in the first embodiment. However, this need not be so, and the first embodiment could use a single composite chamber and the second embodiment could use separate chambers.

Figure 10:
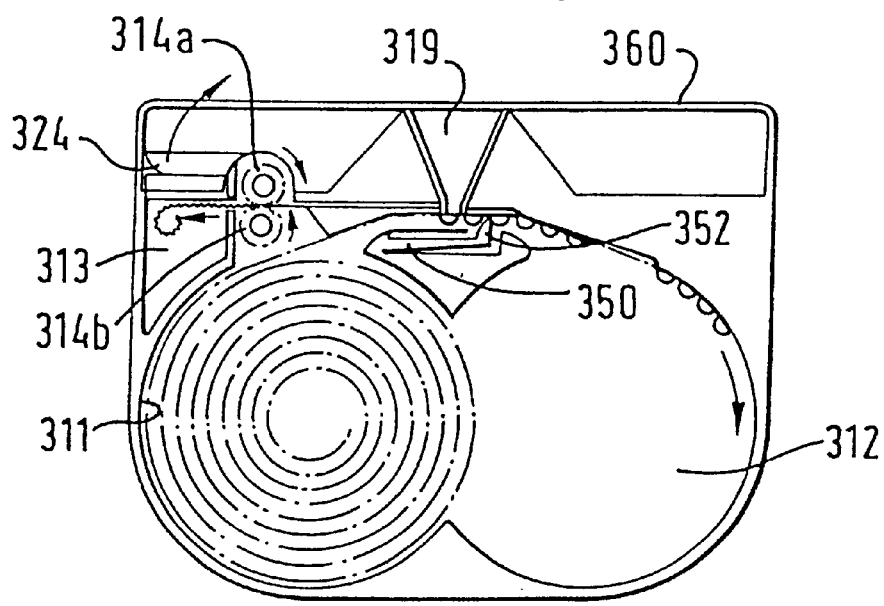
FIG. 10 is a front view of a third embodiment, showing the interior structure thereof.
Figure 11:
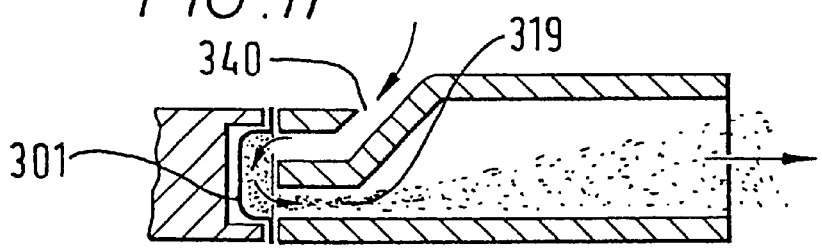
FIG. 11 is an axial view, on a larger scale, showing the mouthpiece of the third embodiment.
Figure 12:
FIG. 12 is a view from below of the third embodiment.

FIGS. 10 to 12 show a third embodiment. In many respects this resembles the second embodiment, and components in the third embodiment which correspond in general terms to components in the second embodiment are denoted by the same reference numerals but with the addition of a further 100.

One difference which will be observed between the second and third embodiments is that in place of the lid wheel 114 a pair of wheels 314a and 314b are employed, with the lid sheet being gripped in the nip between the wheels 314a and 314b, which act as a mangle. These wheels are knurled or otherwise roughened to improve the grip between the wheels and the lid sheet. The used lid sheet is not wound up but is fed into a chamber 313, so that no problem arises, as it does in the first two embodiments, with the lid wheel attempting to wind up progressively longer lengths of lid as operation of the device continues.

FIG. 11 shows the mouthpiece to be of a somewhat different design to that shown in FIGS. 4a and 4b. The mouthpiece is shown as having a single air inlet 340.in place of the pair of air inlets 140, and the powder outlet 119 of FIGS. 4a and 4b is replaced by a mouthpiece portion 319 of reduced width. It should be understood, however, that the device shown in FIGS. 10 to 12 could be modified so as to incorporate a mouthpiece more closely resembling FIGS. 4a and 4b.

FIG. 10 shows the device as being provided with a hinged cover 360, and such cover could be provided for either of the first two embodiments. FIG. 12 shows the device as having a window 370 through which indicia on the strip can be viewed. By printing the strip with numbers or other indicia which correlate with the number of pockets from which powder has been dispensed, or alternatively is to be dispensed, the user is provided with an indication of how many doses have been used or, alternatively, how many doses remain. Another possibility is to use a dose counting device driven by one of the rotating components of the inhalation device. It should be noted that similar indicia and means for viewing those indicia could be provided in all the embodiments.

FIGS. 13 to 16 show a further embodiment of the invention. This is similar in the principle of its operation to the first embodiment, and components in the fourth embodiment which correspond in general terms to components in the first embodiment are denoted by the same reference numerals but with the addition of 400.

Figure 35:
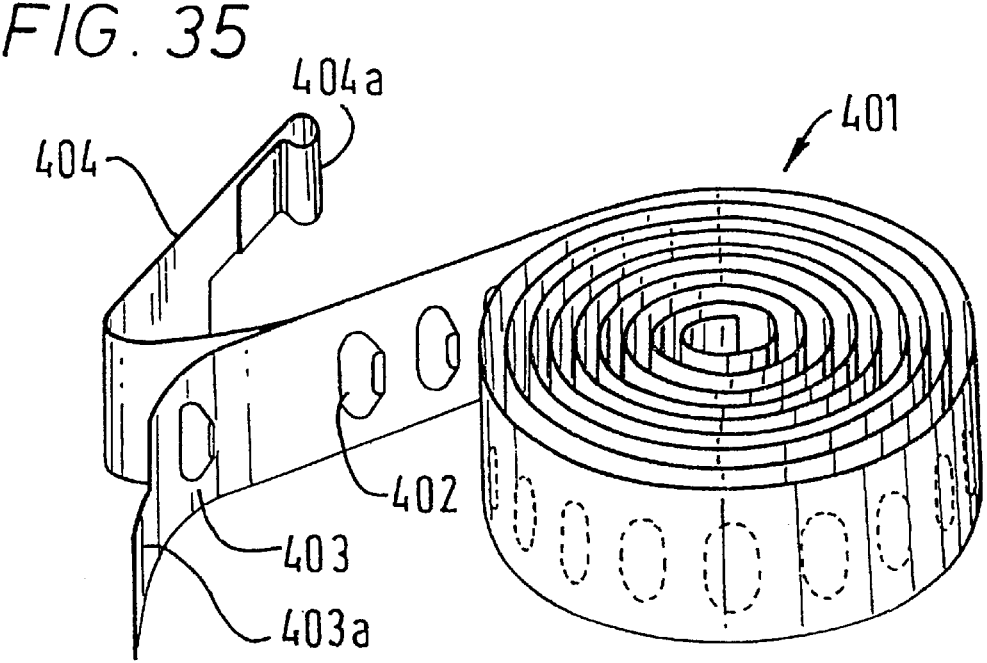
FIG. 35 is a perspective view on a larger scale showing an embodiment of medicament pack according to the invention.

As in the first embodiment, the device receives a flexible strip, here denoted as 401, comprising a base sheet 403 in which pockets 402 are defined and a lid sheet 404. The strip 401, is shown most clearly in. FIG. 35. The lid sheet 404 has a loop 404a formed at the leading end thereof for engagement over a post 471a extending upwardly from a toothed wheel 471 (described below). The base sheet has a lead portion 403a of reduced width for engagement in a slot 470a formed in the base winding wheel 470 (described below). The leading end portions of the base sheet and lid sheet are not sealed together, as can be seen in FIG. 35.

The body 410 comprises a base 410a and a top 410b both of generally circular shape. When the device is assembled the base and top are snap-fitted together. The body defines a single internal chamber within which the strip 401 is housed and within which are also housed a wheel 414 for winding up the used portion of the lid sheet 404, a base winding wheel 470 and an index wheel 416. The index wheel 416 is hollow and an index ratchet wheel 422 is housed within it. All the wheels just mentioned are mounted in the chamber defined by the body, for rotational movement with respect thereto. A pawl 470b is attached to the body 410 and engages the teeth of the base winding wheel 470 to prevent the wheel moving anticlockwise, thus ensuring that the strip 401 can only proceed forwards through the device.

The lid winding wheel 414 is formed in two parts, namely a toothed wheel 471 having teeth 472 and a shaft 473, and a collapsible wheel 474 having a hollow central shaft 475 and a plurality of resilient arms 476, for example, as shown, eight such arms, extending from the central shaft 475 each at an angle to a radius. The toothed wheel 471 has a lug 477 which engages in a corresponding notch in the shaft 475 so that the wheels 471 and 474 rotate in unison.

The hollow index wheel 416 has external teeth 478 which mesh with the teeth of the base winding wheel 470 and the teeth of the wheel 471. Ratchet teeth 479 are formed on the internal walls of the index wheel 416, and the index ratchet wheel 422 has two pawls 480 which engage the ratchet teeth 479.

The device further comprises a lever 424 which comprises an arcuate wall 481 with a finger tab 482, and an arm 483 which extends inwardly from the wall 481 and carries an arcuate array of teeth 484 at its distal end. The lever is pivotally mounted to the centre of the base 410a for movement about an axis which is at the centre of the pitch circle of the teeth 484, the teeth 484 mesh with the teeth 485 on the index ratchet wheel 422.

A manifold 486 provides communication between the chamber within the body 410 and a mouthpiece 420. The manifold has a powder outlet 419 and also has a passageway 487 to allow used lid strip 404 to pass to the collapsible wheel 474. Optionally, a roller 488 may be provided to guide the strip 404 into the passageway 487.

A dose monitor ring 489 having teeth 490 is arranged to be rotatable within the body base 410a. On its lower surface this bears indicia (not visible in the drawings) which can be viewed by the user through a window 494 in the body 410. It will be noted from FIGS. 16a to 16d that the window can be seen both when the cover 491 (see below) is closed and when it is open. The indicia indicate either exactly or approximately the number of doses left (or the number of doses used, if preferred). The ring 489 is rotated by virtue of the fact that its teeth 490 are engaged by the teeth 478 of the index wheel.

The device is provided under a cover 491 which is pivotally mounted on the body 410 by means of a lug 492 on the body top. 410b and a corresponding lug 493 on the body base 410a. The cover is pivotal between an open position (shown in FIG. 14) in which the mouthpiece is exposed and a closed position in which it is not, as is described more fully below.

In operation, the user moves the cover 491 to its open position and then presses on the finger tab 482 of the lever 424 to cause it to move as the lever pivots. This makes the index ratchet wheel 422 rotate which, via the pawls 480, causes the index wheel 416 also to rotate. Rotation of the index wheel 416 produces rotation of both the base winding wheel 470 and the lid winding wheel 414, thus peeling the base sheet and lid sheet apart over a distance sufficient to expose a previously unopened pocket 402 opposite the end of the powder outlet 419 in the manifold 486. The patient can then inhale through the mouthpiece, as in the preceding embodiments.

Figure 16:
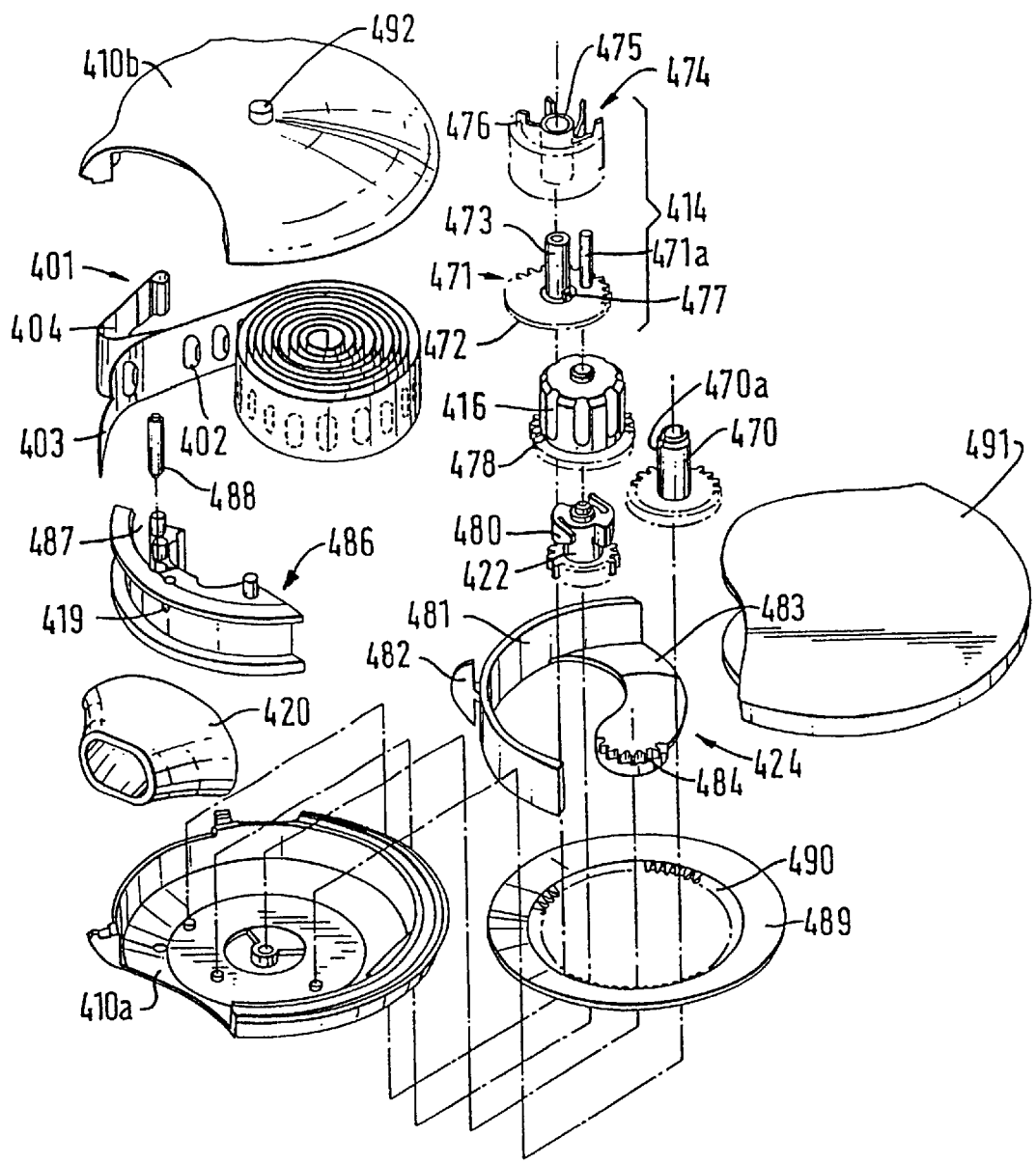
Figure 16A:
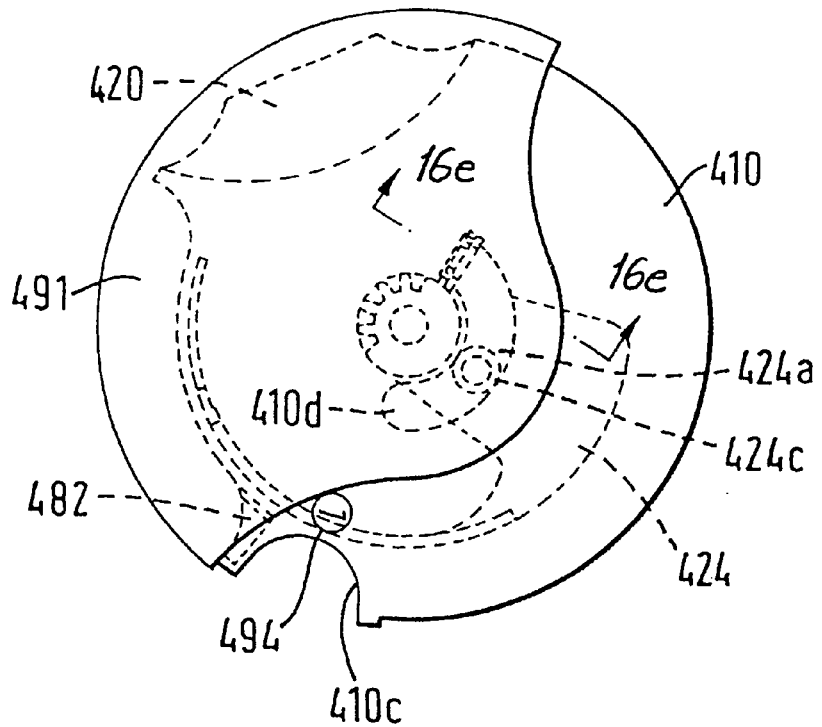
Figure 16B:
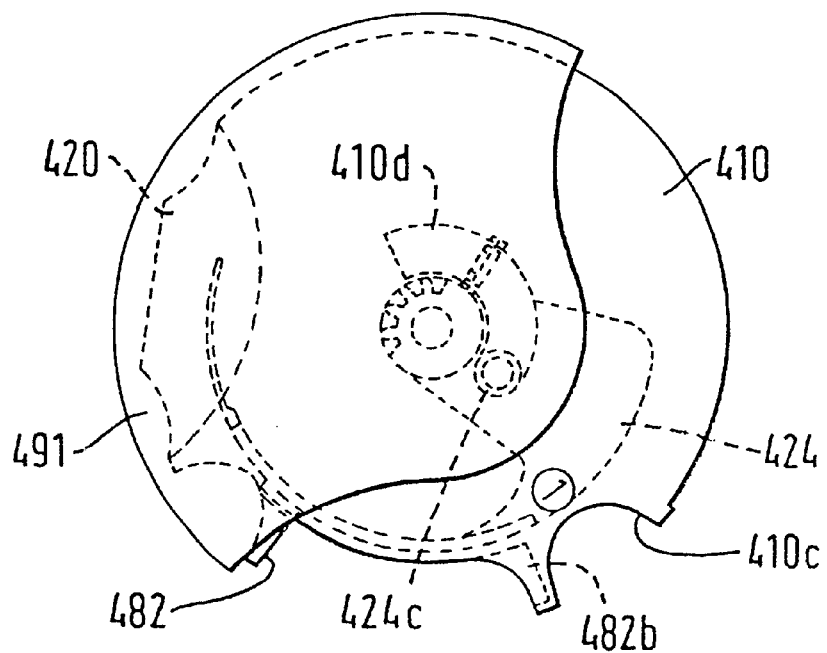
Figure 20:
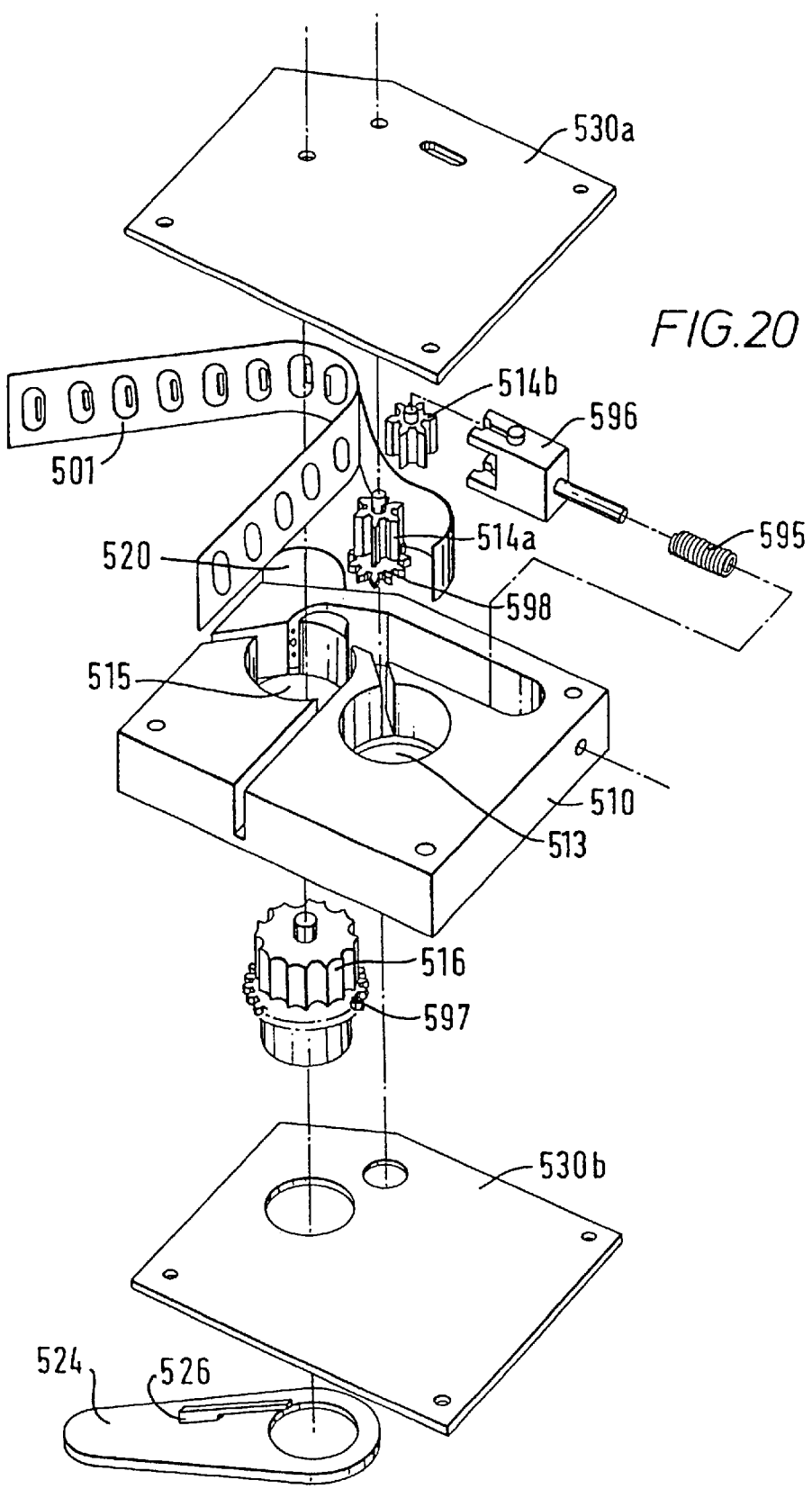
Figure 21:
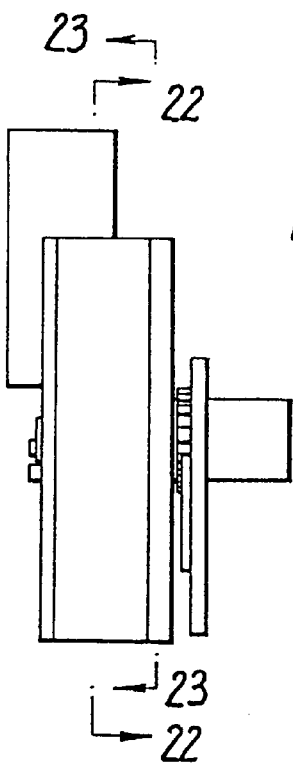
FIGS. 21 to 24 show a sixth embodiment of the invention, FIG. 21 being an end view, FIG. 22 a section on line A—A in FIG. 21, FIG. 23 a section on line B—B in FIG. 21, and FIG. 24 an exploded view.
Figure 22:
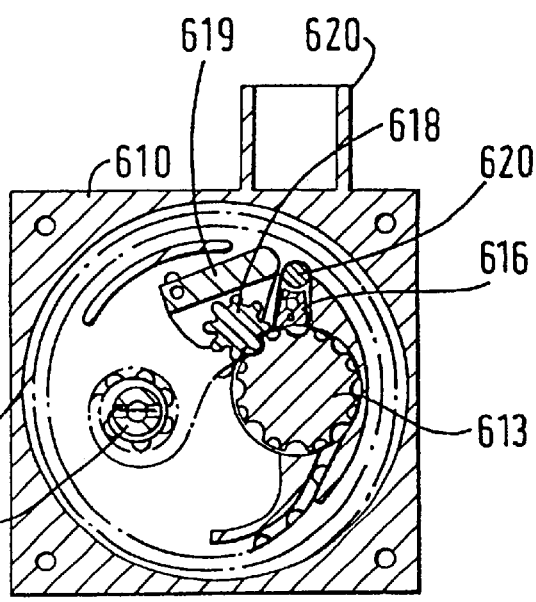
Figure 23:
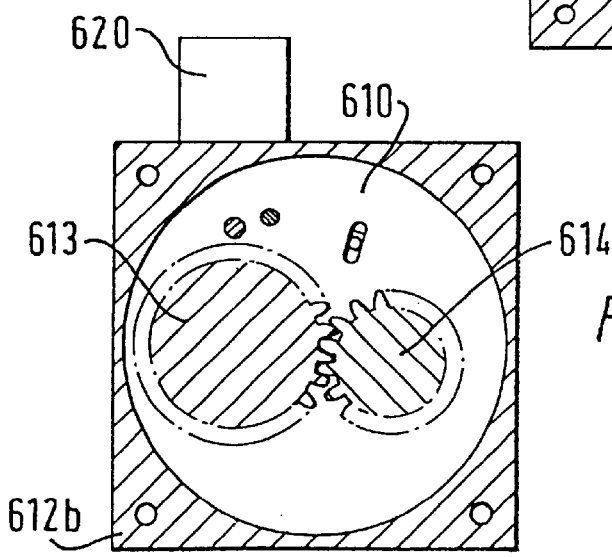
Figure 24:
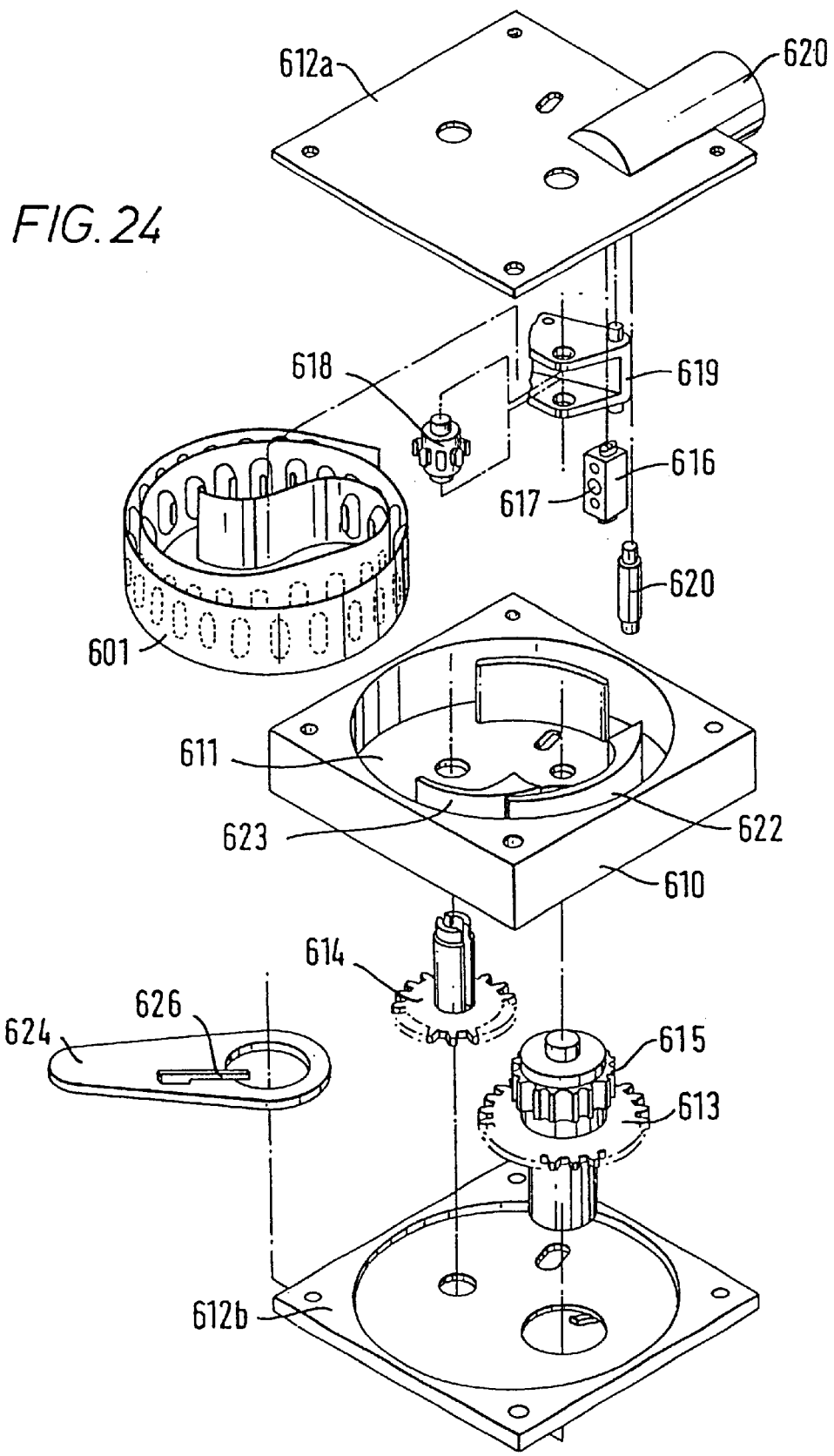
Figure 25:
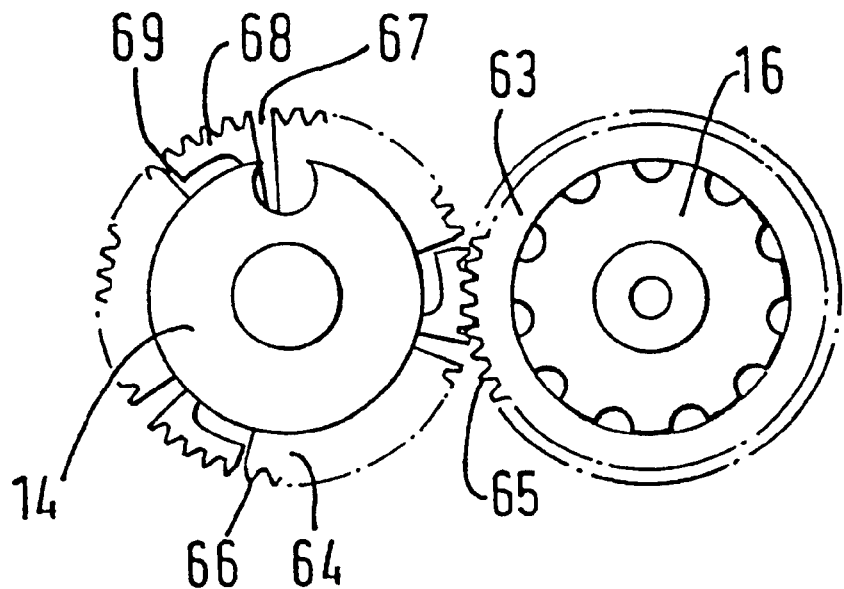
FIGS. 25 to 29 show a modified clutch which may be used in those embodiments of the invention which require it, and are, respectively, a front view, a top view, a back view, a left side view and an axonometric view.
Figure 26:
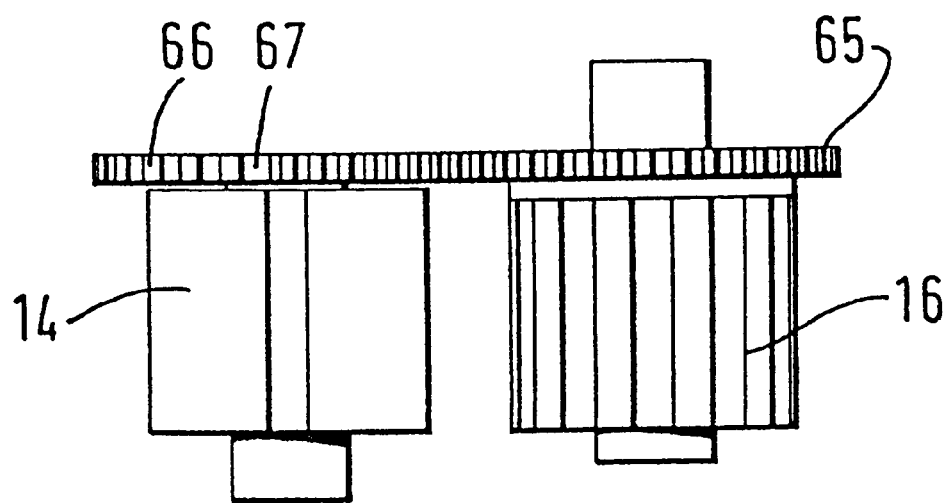
Figure 27:
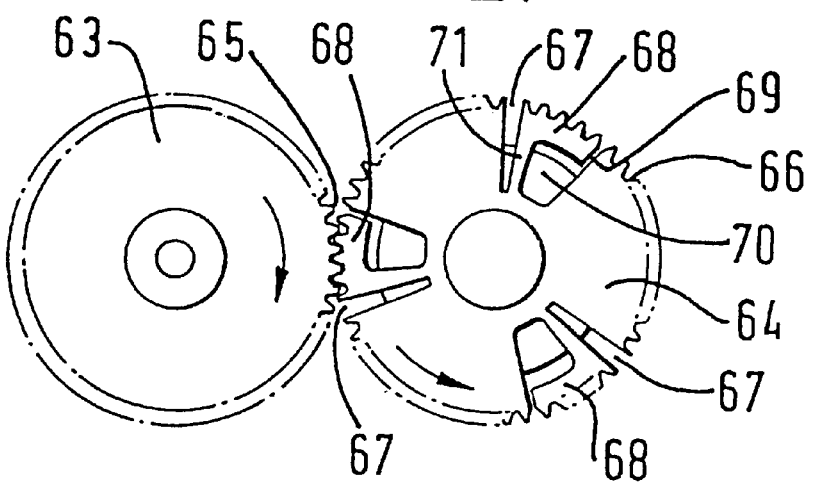
Figure 28:
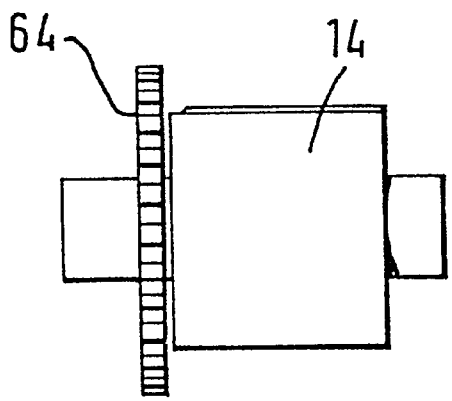
Figure 29:
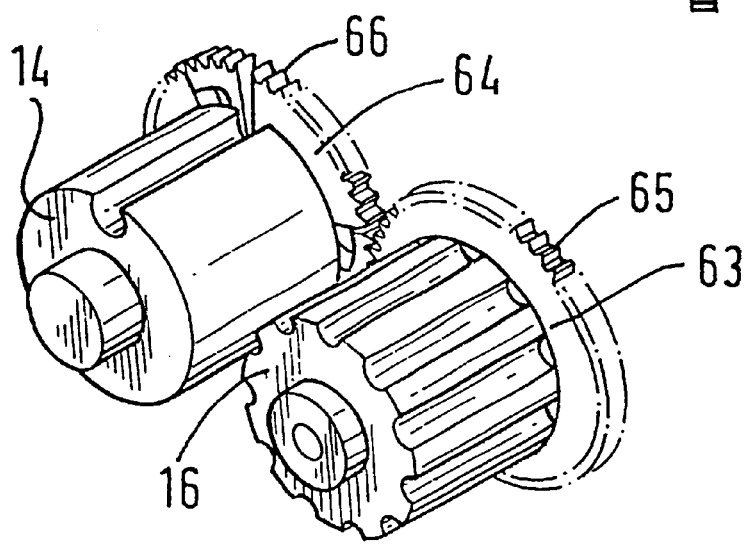

Successive stages in the operation of the device are shown in FIGS. 16a and 16d. The device is in its closed position in FIG. 16a. The finger tab 482 of the lever 424 is at this stage in a recess 482b formed in the body 410 (seen more clearly in FIGS. 16b and 16c). The cover 491 is held stationary as the body 410 is rotated anticlockwise, a recess 410c being provided in the periphery of the body to enable the user to insert a finger for this purpose. The device is thus moved to the partly open position shown in FIG. 16b. During this process the level 424 remains stationary with respect to the cover 491. This is achieved by the lever being provided internally with a resilient arm 424a the tip 424b of which engages in a recess 491a in the cover 491. The arm 424a is attached to the lever 424 via a cylindrical member 424c. As viewed in FIG. 16a, the arm 424a extends anticlockwise from the member 424c over an arc of about 90°. The cylindrical member 424c is guided in an arcuate slot 410d formed in the body 410. The slot 410d extends through an arc of about 180°, and in FIG. 16a the member 424c is shown as being approximately half way along its length. In FIG. 16b it is shown as being at one end.

The user continues to rotate the body 410 from the position shown in FIG. 16b to the position shown in FIG. 16c. During this further rotation tip 424b of the arm 424a jumps out of the recess 491a. This occurs because, with the member 424c at one end of the slot 410d, movement of the body 410 carries the member 424c with it in an anticlockwise direction and hence compels the arm 424a likewise to move anticlockwise. The user then moves the lever 424 by pushing on the finger tab 482 to cause it to rotate anticlockwise through the position shown in FIG. 16c to the position shown in FIG. 16d where the finger tab 482 re-enters the recess 482b. The steps, thus far described both expose the mouthpiece 420 and open a fresh blister. The device is therefore now ready for the user to inhale.

After use, the body 410 is rotated clockwise, the lever 424 moving in unison with the body, to bring the device back to the position of FIG. 16a.

It will be noted that the collapsible wheel 474 in effect assumes the function of the clutch in the first embodiment. As more lid sheet is wound onto the wheel 474 the arms 476 gradually flex inwardly, and the effect is to keep the external diameter of the reel of wound up lid sheet substantially constant, while the internal diameter thereof gradually decreases.

Instead of the wheel 414 with its collapsible wheel 474 it is possible to use the alternative structure shown in. FIG. 30 or that shown in FIGS. 31 and 31a. The principle of operation of the structure shown in FIG. 30 is very similar to that of the clutch arrangement shown in FIGS. 25 to 29. The structure of FIG. 30 comprises two components 800 and 801. The component 800 comprises a generally cylindrical hollow housing 802 open at its lower end and three arcuate arrays of teeth 803. The cylinder 802 has a slot 804 extending through the upper surface thereof, and a post 805 for receiving the leading end of the lid sheet. The component 801 comprises a disc 806 provided with three arcuate arrays of teeth 807, and an upright member 808 extending upwardly from the disc 806. The member 808 is formed of a material, example a plastics material, which is resilient in torsion.

The two components 800 and 801 are snap-fitted together so that the upper end of the member 808 is received in the slot 804 and cannot rotate with respect thereto. The arrays of teeth 803 and 807 are coplanar and alternate with one another. The teeth 803 and 807 mesh with the teeth 478 of the index wheel. Each array 807 is separated from one of the adjacent arrays 803 (but not from the other) by a gap equal to one tooth. Thus, there are three gaps, each of one tooth width, around the assembled arrays. Because the member 808 can flex in torsion, the disc 806 is free to move back and forth between a position in which the gaps are each on one side of a respective array 807 and a position in which the gaps are each on the other side of a respective array 807. This has the effect of producing slippage of the structure shown in FIG. 30 with respect to the index wheel.

Figure 31A:
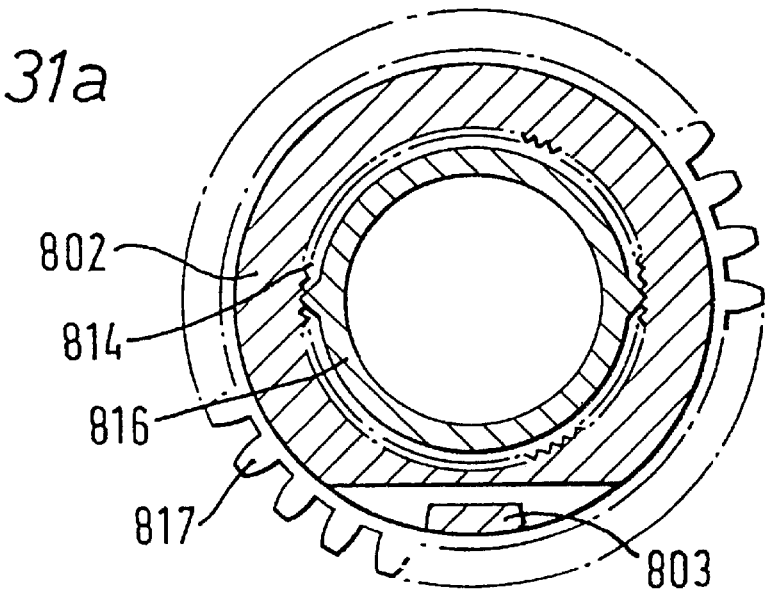
FIG. 31a is transverse section through the clutch shown in FIG. 31.

The structure shown in FIG. 31 is a slipping clutch. It comprises two components 810 and 811, snap-fitted together. The component 810 comprises a generally cylindrical housing 812 open at its lower end and having a post 813 for receiving the leading end of the lid sheet. The interior of the housing 812 is provided with longitudinally extending serrations 814, as can be seen in FIG. 31a. The component 811 comprises a cylinder 815 which extends upwardly from a disc 816 provided with teeth 817. The teeth 817 mesh with the teeth 478 of the index wheel. The cylinder 815 is provided on its outer surface with a pair of pips 818 which are in interfering engagement with the serrations 814. When the rotational force applied by the component 811 to the component 810 is below a predetermined level the components rotate together. However, the cylinder is made of a material, for example a plastics material, which can deform radially, and when the rotational force exceeds the predetermined level such deformation takes place, permitting the pips 818 to move over the serrations 814.

Although in the embodiment of FIGS. 13 to 16, with or without the modifications of FIGS. 30 and 31, the base sheet is wound up as well as the lid sheet, it is not necessary for there also to be a slipping clutch or the like between the index wheel and the base winding wheel. The diameter of the base winding wheel is so chosen that initially the base sheet is wound up only very loosely, and the tightness with which the sheet is wound increases during operation but without ever reaching an unacceptable level. In theory, the base sheet could be wound up precisely via a slipping clutch or the like, with the lid sheet being only loosely wound, but in practice it is much easier to wind up the lid precisely because it is flat and because it is thinner than the base sheet.

FIGS. 17 to 20 show in diagrammatic form the main operative parts of a device which has some similarities to those shown in FIGS. 10 to 12, i.e. it is a mangle device. However, it is to be understood that FIGS. 17 to 20 do not show a complete device, the chamber for the unused strip and the used base material being omitted. Components in this embodiment which correspond in general terms to particular components in the embodiment of FIGS. 10 to 12 are denoted by the same reference numerals, but with the addition of a further 200.

The device of FIGS. 17 to 20 comprises a pair of wheels 514a and 514b which have meshing teeth formed thereon and which act as a mangle engaging the used lid material. This material is fed into a chamber 513. The wheel 514b is an idler wheel and is urged into engagement with the wheel 514a by a compression spring 595 which acts on a carrier 596 which carries the wheel 514b. The wheel 514a has a ring of gear teeth 598 which mesh with teeth 597 formed on an index wheel 516 which performs the same indexing function as the index wheel 16 in the first embodiment and is rotatable in a chamber 515. The chambers are formed in a body 510 and lids 530a and 530b are secured to opposite sides of the chamber. Inhalation is through a mouthpiece 520. The device is operated by a lever 524 which turns the index wheel 516 via a pusher arm 526.

The embodiment shown in FIGS. 21 to 24 is another type of mangle device, but one in which both the lid and base sheets pass through the wheels of the mangle.

The embodiment of FIGS. 21 to 24 comprises a body 610 defining a substantially circular chamber 611 and having lids 612a and 612b secured thereto. Within the chamber 611 an index wheel 613 and a base and lid winding wheel 614 are rotatably mounted, the wheels 613 and 614 having gear teeth which mesh with one another. The index wheel 613 has grooves 615, and a lid gripper wheel 618, rotatably carried in a carrier 619 is also mounted adjacent the grooves 615, downstream of the manifold 616. A roller 620 is mounted behind the manifold 616 to guide the lid sheet.

Flexible strip 601 is provided in the chamber 611, the main part of the strip being initially coiled up around the internal wall of the chamber. The leading end of the strip passes between guide members 622 and 623 over part of the circumference of the index wheel 613, with the powder containing pockets thereof engaged in the grooves 615. At the point where the strip meets the manifold 616 it is peeled apart, and the lid sheet passes behind the manifold and over the roller 620 while the base sheet passes between the index wheel and the manifold. After the manifold both sheets pass between the index wheel and the lid gripper wheel 618, and are gripped thereby. The front end of the strip is fixed in the base and lid winding wheel 614.

In use, the strip 601 is advanced by rotating the index wheel, by means of a lever 624, via a pusher arm 626, which causes corresponding rotation of the base and lid winding wheel. This winds up the base and lid, initially loosely, though increasing in tightness as the operation proceeds, but without, however, the tightness ever reaching an unacceptable level. The lid and base sheets are peeled apart where the strip meets the manifold 616, presenting a fresh pocket of powder to the powder outlet 617. Inhalation is via a mouthpiece 620.

Figure 32:
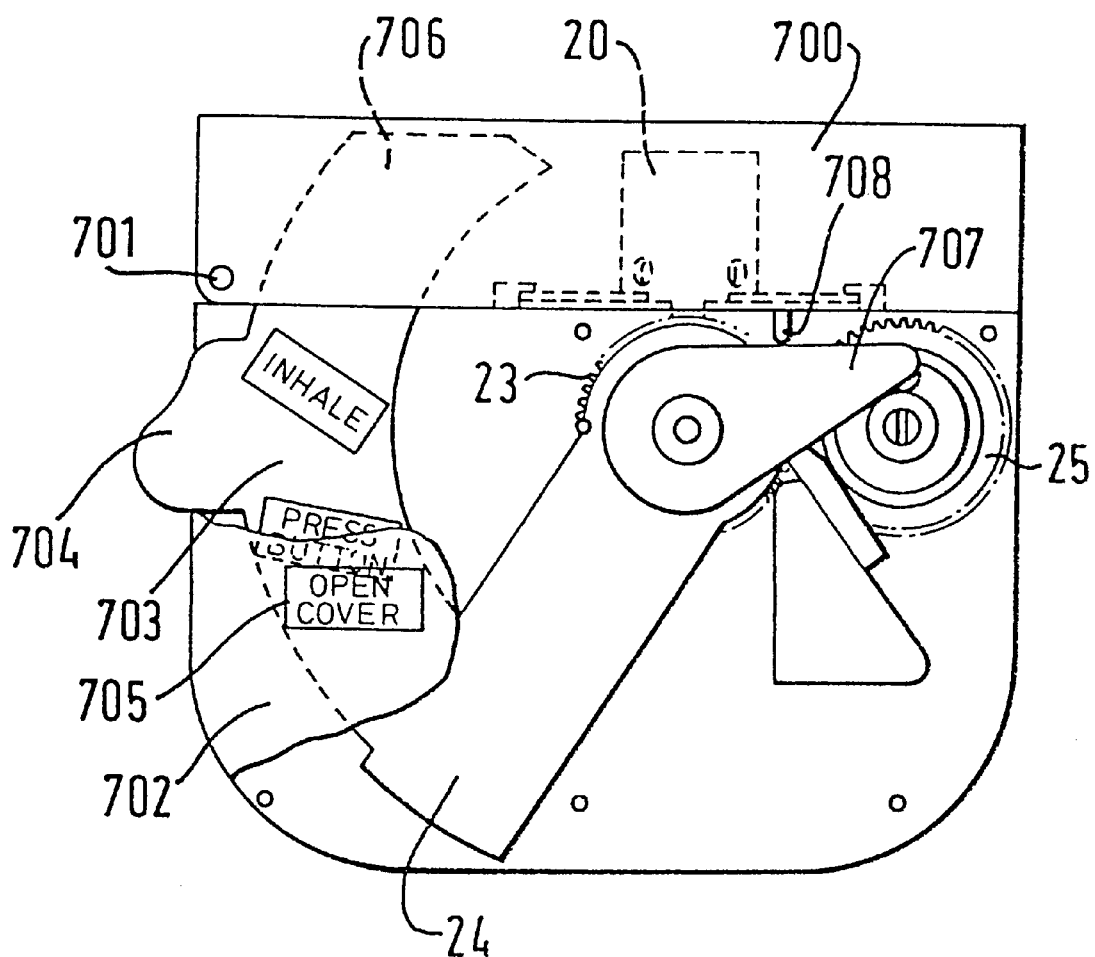

FIGS. 32 to 34 show an embodiment of the invention incorporating, as a further feature, indicia which instruct the user as to the successive steps which the user is to take to operate the device. Apart from the indicia, the device is largely the same as the embodiment shown in FIGS. 1 to 3, and the same reference numerals are used for the corresponding components. However, there are some additional components, as will be apparent from the following description.

The device shown in FIGS. 32 to 34 has a cover 700 which is pivotally connected to the remainder of the device for pivotal movement about an axis 701. The gear wheels 23 and 25 and the associated components are covered by a rear wall 702. This extends over the whole of the rear of the device, but in the drawings all except a small portion thereof is shown broken away for ease of understanding. The lever 24 is provided with an arcuate extension 703, on an edge whereof is formed a cam 704. The extension 703 carries indicia in the form of instructions to the user, in this case the legends "OPEN COVER", "PRESS BUTTON", "INHALE". When the lever 24, and hence the extension 703, are in particular positions a respective one of these legends is visible through a window 705 in the rear wall 702. The distal end of the extension 703 constitutes a button 706. The end of the lever 24 remote from the extension 703 carries a tongue 707 pivotal therewith.

FIG. 32 shows the device in its rest position. The legend "OPEN COVER" is visible through the window 705. If a patient now opens the cover 700 this brings the device into the position shown in FIG. 33. It will be seen that the top rear edge of the cover has struck the cam 704 and moved the extension. 703 through an angle such as to make the legend "PRESS BUTTON" visible through the window 705. If the user now presses the button 706 this causes the lever 24 to rotate, thus opening a powder-containing container, as described in connection with FIGS. 1 to 3. This brings the device into the position shown in FIG. 34, in which the legend "INHALE" is visible through the window 705. It will also be seen that in the position of FIG. 34 the tongue 707 protrudes upwardly. Accordingly, when the user, having inhaled, closes the cover, the tongue 707 is struck by a lug 708 on the underside of the cover, which pushes the lever 24, with its extension 703, back into the position shown in FIG. 32, once again causing the legend "OPEN COVER" to be displayed.

The device just described not only gives the step-by-step instructions to the user, thus reducing the risk of a patient being confused, but also makes it difficult for the patient to use the device other than in the intended manner, by virtue of the fact that the button 706, once depressed, is not again accessible until the user closes the cover and reopens it.

In the embodiments described above, reference is made to a mouthpiece. However, if the device was to be used for purposes other than oral inhalation some other outlet would be employed, e.g. a nosepiece.

What is claimed is:

1. An inhalation device for use with a medicament pack having a plurality of containers for containing medicament in powder form wherein the containers are spaced along the length of and defined between two peelable sheets secured to each other, said inhalation device comprising:

an opening station for receiving a container of a medicament pack being used with said inhalation device;

a peeler positioned to engage peelable sheets of a container which has been received in said opening station so as to peel apart the peelable sheets, opening the container;

an outlet, positioned to be in communication with an opened container, through which a user can inhale medicament in powder form from such an opened container; and an indexer positioned to index in communication with said outlet containers of a medicament pack in use with said inhalation device.

2. A device according to claim 1 adapted for use where one of such peelable sheets is a base sheet having a plurality of pockets therein, and an other of such peelable sheets is a lid sheet, each pocket and an adjacent part of such a lid sheet defining a respective one of such container, said peeler comprising a driver for pulling such a lid sheet and a base sheet apart at the opening station.

3. A device according to claim 2 wherein said indexer is engageable between adjacent pockets to cause each pocket in turn to be positioned in communication with the outlet.

4. A device according to claim 2 comprising at least one chamber for receiving medicament pack before opening, and for receiving the base sheet and lid sheet after peeling apart.

5. A device according to claim 4 further comprising resilient coil-formers for holding in coiled form at least one of: (i) a medicament pack being used with said inhalation device and; (ii) a base sheet of a container which has been received in said opening station.

6. A device according to claim 2 wherein the said driver comprises a lid driver for pulling such a lid sheet.

7. A device according to claim 6 wherein the lid driver comprises a pair of driving wheels which drivingly engage such a lid sheet between them.

8. A device according to claim 6 wherein the said driving wheels are toothed wheels having interengaging teeth.

9. A device according to claim 6 comprising a rotatable index wheel having recesses therein, the wheel being engageable with such a medicament pack so that the recesses each receive a respective pocket.

10. A device according to claim 9 wherein the index wheel and the lid driver are interconnected so that the rotation of one correlates with the rotation of the other.

11. A device according to claim 1 operable in a plurality of steps, which comprises an indicator adapted to display to a user an instruction as to the next step once the preceding step has been taken.

12. A device according to claim 11 wherein the indicator comprises an indicator member which carries a plurality of legends each constituting an instruction to the user, the indicator member being movable by a given step being carried out to display the legend relating to the next step.

13. An inhalation device for opening a medicament pack having a plurality of containers for containing medicament in powder form wherein the containers are defined between an elongate base sheet and an elongate lid sheet peelably secured to each other with the base sheet having a plurality of pockets therein, said inhalation device comprising:

an opening station for receiving a container of a medicament pack being used with said inhalation device;

a peeler positioned to engage a base sheet and a lid sheet of a container which has been received in said opening station so as to peel apart such a base sheet and lid sheet, to open such a container, said peeler including a lid driver for pulling apart a lid sheet and a base sheet of a container that has been received at said opening station;

an outlet, positioned to be in communication with an opened container, through which a user can inhale medicament in powder form from such an opened container; and an indexer for indexing a communication with said outlet containers of a medicament pack in use with said inhalation device, said indexer including a rotatable index wheel having recesses therein, said index wheel being engageable with a medicament pack in use with said inhalation device such that said recesses each receive a respective pocket of a base sheet of a medicament pack in use with said inhalation device, said index wheel and lid driver being interconnected by a slipping clutch so that the rotation of one correlates with the rotation of the other.

14. A device according to claim 13 wherein the slipping clutch comprises a first gear member which is movable with the index wheel and has a toothed surface, and a second toothed gear member which is movable with the lid driver and has a toothed surface in meshing engagement with the toothed surface of the said first gear member, at least one of the toothed surfaces having a toothed portion which is movable back and forth with respect to the remainder of the toothed surface of which it is part.

15. A device according to claim 13 wherein the slipping clutch comprises a first clutch member movable with the index wheel and a second clutch movable with the lid driver, one of the clutch members comprising an annular array of serrations and the other of the clutch members being adapted to grippingly engage the serrations when less than a predetermined force is applied between the two clutch members and which slip with respect to the serrations when a force equal to or greater than the predetermined force is applied.

16. An inhalation device for opening a medicament pack having a plurality of containers for containing medicament in powder form wherein the containers are defined between an elongate base sheet and an elongate lid sheet peelably secured to each other with the base sheet having a plurality of pockets therein, said inhalation device comprising:

an opening station for receiving a container of a medicament pack being used with said inhalation device;

a peeler positioned to engage a base sheet and a lid sheet of a container which has been received in said opening station so as to peel apart such a base sheet and lid sheet, to open such a container, said peeler including a lid driver for pulling apart a lid sheet and a base sheet of a container that has been received at said opening station;

an outlet, positioned to be in communication with an opened container, through which a user can inhale medicament in powder form from such an opened container;

an indexer positioned to index in communication with said outlet containers of a medicament pack in use with said inhalation device, said indexer including a rotatable index wheel having recesses therein, said index wheel being engageable with a medicament pack in use with said inhalation device such that said recesses each receive a respective pocket of a base sheet of a medicament pack in use with said inhalation device, said index wheel and lid driver being interconnected by a slipping clutch so that the rotation of one correlates with the rotation of the other; and said lid driver comprising a wheel on which a lid sheet of a medicament pack in use with said inhalation device is wound up, said wheel having a winding surface which decreases in diameter when tension in said lid sheet increases.

17. A device according to claim 16 wherein the said wheel comprises a plurality of resiliently flexible arms each extending therefrom at an angle with respect to a radius.

18. An inhalation device for opening a medicament pack having a plurality of containers for containing medicament in powder form wherein the containers are defined between an elongate base sheet and an elongate lid sheet peelably secured to each another with the base sheet having a plurality of pockets therein, said inhalation device comprising:

an opening station for receiving a container of a medicament pack being used with said inhalation device;

a peeler positioned to engage a base sheet and a lid sheet of a container which has been received in said opening station for peeling apart such a base sheet and lid sheet to open such a container, said peeler including a driver for pulling apart a lid sheet and a base sheet of a container that has been received at said opening station;

an outlet positioned to be in communication with an opened container through which a user can inhale medicament in powder form from such an opened container;

an indexer for indexing in communication with said outlet containers of a medicament pack in use with said inhalation device, said indexer including, a guide for guiding such a lid sheet and base sheet along separate paths at said opening station, said paths reuniting downstream of said opening station, said driver being located after the point where said paths reunite and being operable to drive both a lid sheet and a base sheet.

19. A device according to claim 18 wherein the said driver comprises a pair of toothed wheels having interengaging teeth.

20. In combination an inhalation device and a medicament pack received therein, in which said medicament pack comprises:

a strip formed from a base sheet having a plurality of recesses and a lid sheet hermetically but peelably sealed thereto to define a plurality of containers, each container having therein inhalable medicament in powder form;

and said inhalation device comprises:

an opening station for receiving a container of said medicament pack;

peeling means positioned to engage peelable sheets of a container which has been received in said opening station for peeling apart the peelable sheets to open the container;

an outlet positioned to be in communication with an opened container through which a user can inhale the medicament in powder form from the opened container; and indexing means for indexing communication with said outlet containers of said medicament pack.

21. An inhalation device for use with a medicament pack having a plurality of containers for containing medicament in powder form wherein the containers are defined between two peelable sheets secured to each other, said inhalation device comprising:

an opening station for receiving a container of a medicament pack being used with said inhalation device;

a peeler positioned to engage peelable sheets of a container which has been received in said opening station so as to peel apart the peelable sheets, opening the container;

an outlet, positioned to be in communication with an opened container, through which a user can inhale medicament in powder form from such an opened container; and an indexer positioned to index in communication with said outlet containers of a medicament pack in use with said inhalation device.

22. An inhalation device for opening a medicament pack having a plurality of containers for containing medicament in powder form wherein the containers are defined between a base sheet and a lid sheet peelably secured to each other with the base sheet having a plurality of pockets therein, said inhalation device comprising:

an opening station for receiving a container of a medicament pack being used with said inhalation device;

a peeler positioned to engage a base sheet and a lid sheet of a container which has been received in said opening station so as to peel apart such a base sheet and lid sheet, to open such a container, said peeler including a lid driver for pulling apart a lid sheet and a base sheet of a container that has been received at said opening station;

an outlet, positioned to be in communication with an opened container, through which a user can inhale medicament in powder form from such an opened container; and an indexer for indexing in communication with said outlet containers of a medicament pack in use with said inhalation device, said indexer including a rotatable index wheel having recesses therein, said index wheel being engageable with a medicament pack in use with said inhalation device such that said recesses each receive a respective pocket of a base sheet of a medicament pack in use with said inhalation device, said index wheel and lid driver being interconnected by a slipping clutch so that the rotation of one correlates with the rotation of the other.

23. An inhalation device for opening a medicament pack having a plurality of containers for containing medicament in powder form wherein the containers are defined between a base sheet and a lid sheet peelably secured to each other with the base sheet having a plurality of pockets therein, said inhalation device comprising:

an opening station for receiving a container of medicament pack being used with said inhalation device;

a peeler positioned to engage a base sheet and a lid sheet of a container which has been received in said opening station so as to peel apart such a base sheet and lid sheet, to open such a container, said peeler including a lid driver for pulling apart a lid sheet and a base sheet of a container that has been received at said opening station;

an outlet, positioned to be in communication with an opened container, through which a user can inhale medicament in powder form from such an opened container;

an indexer positioned to index in communication with said outlet containers of a medicament pack in use with said inhalation device, said indexer including a rotatable index wheel having recesses therein, said index wheel being engageable with a medicament pack in use with said inhalation device such that said recesses each receive a respective pocket of a base sheet of a medicament pack in use with said inhalation device, said index wheel and lid driver being interconnected by a slipping clutch so that the rotation of one correlates with the rotation of the other; and said lid driver comprising a wheel on which a lid sheet of a medicament pack in use with said inhalation device is wound up, said wheel having a winding surface which decreases in diameter when tension in said lid sheet increases.

24. An inhalation device for opening a medicament pack having a plurality of containers for containing medicament in powder form wherein the containers are defined between a base sheet and a lid sheet peelably secured to each other with the base sheet having a plurality of pockets therein, said inhalation device comprising:

an opening station for receiving a container of a medicament pack being used with said inhalation device;

a peeler positioned to engage a base sheet and a lid sheet of a container which has been received in said opening station for peeling apart such a base sheet and lid sheet to open such a container, said peeler including a driver for pulling apart a lid sheet and a base sheet of a container that has been received at said opening station;

an outlet positioned to be in communication with an opened container through which a user can inhale medicament in powder form from such an opened container;

an indexer for indexing in communication with said outlet containers of a medicament pack in use with said inhalation device, said indexing means including, a guide for guiding such a lid sheet and base sheet along separate paths at said opening station, said paths reuniting downstream of said opening station, said driver being located after the point where said paths reunite and being operable to drive both a lid sheet and a base sheet.

25. In combination, an inhalation device and a medicament pack received therein, said medicament pack being formed from a base sheet having a plurality of recesses and a lid sheet peelably sealed in superposed relationship thereto to define a plurality of containers, each having therein inhalable medicament in powder form; and said inhalation device comprising:
an opening station receiving a container of said medicament pack;
a peeler positioned to engage peelable sheets of a container which has been received in said opening station so as to peel apart the peelable sheets, opening the container; and
an outlet positioned in communication with an opened container through which a user can inhale the medicament in powder form from the opened container.

26. A medicament pack for use in an inhalation device, the pack being formed from a base sheet having a plurality of recesses and a lid sheet hermetically but peelably sealed thereto to define a plurality of containers, each container having therein inhalable medicament in powder form.

* * * * *